US008187270B2

(12) United States Patent
Auth et al.

(10) Patent No.: US 8,187,270 B2
(45) Date of Patent: May 29, 2012

(54) HEMOSTATIC SPARK EROSION TISSUE TUNNEL GENERATOR WITH INTEGRAL TREATMENT PROVIDING VARIABLE VOLUMETRIC NECROTIZATION OF TISSUE

(75) Inventors: David C. Auth, Kirkland, WA (US); Alexander Lebedev, Seattle, WA (US); Michael J. Connolly, Bothell, WA (US)

(73) Assignee: Mirabilis Medica Inc., Bothell, WA (US)

( * ) Notice: Subject to any disclaimer, the term of this patent is extended or adjusted under 35 U.S.C. 154(b) by 1205 days.

(21) Appl. No.: 11/936,748

(22) Filed: Nov. 7, 2007

(65) Prior Publication Data
US 2009/0118729 A1 May 7, 2009

(51) Int. Cl.
*A61B 18/14* (2006.01)
(52) U.S. Cl. ............... 606/42; 606/41; 606/45
(58) Field of Classification Search .......... 606/41–45
See application file for complete search history.

(56) References Cited

U.S. PATENT DOCUMENTS

| | | |
|---|---|---|
| 3,470,868 A | 10/1969 | Krause |
| 3,480,002 A | 11/1969 | Flaherty |
| 3,676,584 A | 7/1972 | Plakas |
| 3,941,112 A | 3/1976 | Habert |
| 4,059,098 A | 11/1977 | Murdock |
| 4,097,835 A | 6/1978 | Green |
| 4,185,502 A | 1/1980 | Frank |
| 4,282,755 A | 8/1981 | Gardineer |
| 4,347,850 A | 9/1982 | Kelly-Fry |
| 4,484,569 A | 11/1984 | Driller |
| 4,682,596 A * | 7/1987 | Bales et al. .......... 606/39 |
| 4,742,829 A | 5/1988 | Law |
| 4,756,313 A | 7/1988 | Terwilliger |
| 4,835,689 A | 5/1989 | O'Donnell |

(Continued)

FOREIGN PATENT DOCUMENTS

EP 0301360 B1 2/1989

(Continued)

OTHER PUBLICATIONS

International Search Report mailed Dec. 18, 2009, in corresponding International Application No. PCT/US2009/042303, filed Apr. 30, 2009.

(Continued)

*Primary Examiner* — Linda Dvorak
*Assistant Examiner* — Amanda Scott
(74) *Attorney, Agent, or Firm* — Christensen O'Connor Johnson Kindness PLLC

(57) ABSTRACT

A catheter for insertion into and treatment of tissue in a patient comprises a radio frequency (RF) electrode having an elongated body that conducts electrical RF energy to a conductive tip. An insulating sleeve surrounding the elongated body prevents leakage of RF energy from the elongated body when the catheter is being inserted into the tissue of the patient. In a first mode of operation, the conductive tip is exposed outside the insulating sleeve and the RF electrode delivers first RF energy capable of producing sparks that erode the tissue of the patient and create a tunnel through which the catheter can advance into the tissue of the patient. In a second mode of operation, the insulating sleeve is retracted to expose a portion of the RF electrode. Second RF energy is delivered to the volume of tissue around the catheter to necrotize the tissue by heating without producing sparks.

32 Claims, 10 Drawing Sheets

U.S. PATENT DOCUMENTS

| | | | |
|---|---|---|---|
| 4,858,613 A | 8/1989 | Fry | |
| 4,865,042 A | 9/1989 | Umemura | |
| 4,893,624 A | 1/1990 | Lele | |
| 5,005,579 A | 4/1991 | Wurster | |
| 5,036,855 A | 8/1991 | Fry | |
| 5,080,101 A | 1/1992 | Dory | |
| 5,080,102 A | 1/1992 | Dory | |
| 5,080,660 A | 1/1992 | Buelna | |
| 5,103,804 A * | 4/1992 | Abele et al. | 600/116 |
| 5,117,832 A | 6/1992 | Sanghvi | |
| 5,234,429 A | 8/1993 | Goldhaber | |
| 5,271,402 A | 12/1993 | Yeung | |
| 5,391,140 A | 2/1995 | Schaetzle | |
| 5,441,499 A | 8/1995 | Fritzsch | |
| 5,471,988 A | 12/1995 | Fujio | |
| 5,474,071 A | 12/1995 | Chapelon | |
| 5,492,126 A | 2/1996 | Hennige | |
| 5,520,188 A | 5/1996 | Hennige | |
| 5,520,684 A * | 5/1996 | Imran | 606/41 |
| 5,558,092 A | 9/1996 | Unger | |
| 5,619,999 A | 4/1997 | Von Behren | |
| 5,666,954 A | 9/1997 | Chapelon | |
| 5,720,287 A | 2/1998 | Chapelon | |
| 5,762,066 A | 6/1998 | Law | |
| 5,769,790 A | 6/1998 | Watkins | |
| 5,810,007 A | 9/1998 | Holupka | |
| 5,882,302 A | 3/1999 | Driscoll, Jr. | |
| 5,957,922 A * | 9/1999 | Imran | 606/41 |
| 5,976,092 A | 11/1999 | Chinn | |
| 5,993,389 A | 11/1999 | Driscoll, Jr. | |
| 6,002,251 A | 12/1999 | Sun | |
| 6,007,499 A | 12/1999 | Martin | |
| 6,042,556 A | 3/2000 | Beach | |
| 6,050,943 A | 4/2000 | Slayton | |
| 6,068,653 A | 5/2000 | LaFontaine | |
| 6,083,159 A | 7/2000 | Driscoll, Jr. | |
| 6,126,607 A | 10/2000 | Whitmore, III | |
| 6,196,972 B1 | 3/2001 | Moehring | |
| 6,217,530 B1 | 4/2001 | Martin | |
| 6,254,601 B1 | 7/2001 | Burbank | |
| 6,267,734 B1 | 7/2001 | Ishibashi | |
| 6,315,741 B1 | 11/2001 | Martin | |
| 6,390,973 B1 | 5/2002 | Ouchi | |
| 6,425,867 B1 | 7/2002 | Vaezy | |
| 6,432,067 B1 | 8/2002 | Martin | |
| 6,451,013 B1 | 9/2002 | Bays | |
| 6,461,314 B1 | 10/2002 | Pant | |
| 6,488,639 B1 | 12/2002 | Ribault | |
| 6,500,133 B2 | 12/2002 | Martin | |
| 6,537,224 B2 | 3/2003 | Mauchamp | |
| 6,602,251 B2 | 8/2003 | Burbank | |
| 6,613,004 B1 | 9/2003 | Vitek | |
| 6,626,855 B1 | 9/2003 | Weng | |
| 6,633,658 B1 | 10/2003 | Dabney | |
| 6,645,162 B2 | 11/2003 | Friedman | |
| 6,666,835 B2 | 12/2003 | Martin | |
| 6,676,601 B1 | 1/2004 | Lacoste | |
| 6,692,450 B1 | 2/2004 | Coleman | |
| 6,716,184 B2 | 4/2004 | Vaezy | |
| 6,719,694 B2 | 4/2004 | Weng | |
| 6,740,082 B2 | 5/2004 | Shadduck | |
| 6,764,488 B1 | 7/2004 | Burbank | |
| 6,840,936 B2 | 1/2005 | Sliwa, Jr. | |
| 6,855,143 B2 * | 2/2005 | Davison et al. | 606/41 |
| 6,936,046 B2 | 8/2005 | Hissong | |
| 7,063,666 B2 | 6/2006 | Weng | |
| 7,105,007 B2 | 9/2006 | Hibler | |
| 7,175,596 B2 | 2/2007 | Vitek | |
| 7,258,674 B2 | 8/2007 | Cribbs | |
| 7,452,357 B2 | 11/2008 | Voegele | |
| 7,470,241 B2 | 12/2008 | Weng | |
| 7,473,224 B2 | 1/2009 | Makin | |
| 7,699,782 B2 | 4/2010 | Angelsen | |
| 2001/0012934 A1 * | 8/2001 | Chandrasekaran et al. | 606/41 |
| 2002/0029036 A1 | 3/2002 | Goble | |
| 2002/0065512 A1 | 5/2002 | Fjield | |
| 2002/0120259 A1 | 8/2002 | Lettice | |
| 2003/0004439 A1 | 1/2003 | Pant | |
| 2003/0060736 A1 | 3/2003 | Martin | |
| 2003/0233045 A1 | 12/2003 | Vaezy | |
| 2004/0030269 A1 | 2/2004 | Horn | |
| 2004/0082859 A1 | 4/2004 | Schaer | |
| 2004/0147917 A1 | 7/2004 | Mueller, Jr. | |
| 2004/0153126 A1 | 8/2004 | Okai | |
| 2004/0242999 A1 | 12/2004 | Vitek | |
| 2004/0243201 A1 | 12/2004 | Goldman | |
| 2005/0038340 A1 | 2/2005 | Vaezy | |
| 2005/0085726 A1 | 4/2005 | Lacoste | |
| 2005/0101854 A1 | 5/2005 | Larson | |
| 2005/0154431 A1 | 7/2005 | Quistgaard | |
| 2005/0203399 A1 | 9/2005 | Vaezy | |
| 2005/0256405 A1 | 11/2005 | Makin | |
| 2005/0267454 A1 | 12/2005 | Hissong | |
| 2006/0004351 A1 | 1/2006 | Arless | |
| 2006/0052701 A1 | 3/2006 | Carter | |
| 2006/0094930 A1 | 5/2006 | Sparks | |
| 2006/0264748 A1 | 11/2006 | Vaezy | |
| 2007/0055223 A1 * | 3/2007 | Eckhouse et al. | 606/28 |
| 2007/0066990 A1 | 3/2007 | Marsella | |
| 2007/0194658 A1 | 8/2007 | Zhang | |
| 2007/0197918 A1 | 8/2007 | Vitek | |
| 2007/0238994 A1 | 10/2007 | Stecco | |
| 2008/0039724 A1 | 2/2008 | Seip | |
| 2008/0071165 A1 | 3/2008 | Makin | |
| 2008/0086036 A1 | 4/2008 | Hartley | |
| 2008/0125771 A1 | 5/2008 | Lau | |
| 2008/0221647 A1 | 9/2008 | Chamberland | |
| 2008/0281314 A1 | 11/2008 | Johnson | |
| 2008/0319436 A1 | 12/2008 | Daniel | |
| 2009/0036774 A1 | 2/2009 | Weng | |
| 2009/0228001 A1 | 9/2009 | Pacey | |
| 2009/0326420 A1 | 12/2009 | Moonen | |

FOREIGN PATENT DOCUMENTS

| | | | |
|---|---|---|---|
| EP | 0614651 A1 | 9/1994 | |
| EP | 0734742 A2 | 10/1996 | |
| EP | 1 726 267 A2 | 11/2006 | |
| JP | 405023336 A | 2/1993 | |
| WO | 93/17646 A2 | 9/1993 | |
| WO | 94/27502 A1 | 12/1994 | |
| WO | 95/20360 A1 | 8/1995 | |
| WO | 97/00646 A1 | 1/1997 | |
| WO | 01/71380 A2 | 9/2001 | |
| WO | 2004/073524 A1 | 9/2004 | |
| WO | 2005/000097 A2 | 1/2005 | |
| WO | 2006097661 A1 | 9/2006 | |

OTHER PUBLICATIONS

Daum, D.R., and K. Hynynen, "A 256-Element Ultrasonic Phased Array System for the Treatment of Large Volumes of Deep Seated Tissue," IEEE Transactions on Ultrasonics, Ferroelectrics, and Frequency Control 46(5):1254-1268, Sep. 1999.

Enholm, J.K., et al., "Improved Volumetric MR-HIFU Ablation by Robust Binary Feedback Control," IEEE Transactions on Biomedical Engineering 57(1):103-113, Jan. 2010.

Mougenot, C., et al., "Automatic Spatial and Temporal Temperature Control for MR-Guided Focused Ultrasound Using Fast 3D MR Thermometry and Multispiral Trajectory of the Focal Point," Magnetic Resonance in Medicine 52:1005-1015, 2004.

Mougenot, C., et al., "Three-Dimensional Spatial and Temporal Temperature Control With MR Thermometry-Guided Focused Ultrasound (MRgHIFU)," Magnetic Resonance in Medicine 61:603-614, 2009.

Ngo, F.C., et al., "An Experimental Analysis of a Sector-Vortex Phased Array Prototype," Ultrasonics Symposium Proceedings, 1989, pp. 999-1002.

Rabkin, B.A., et al., "Hyperecho in Ultrasound Images of HIFU Therapy: Involvement of Cavitation," Ultrasound in Medicine and Biology 31(7):947-956, Jul. 2005.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control 39(1):32-38, Jan. 1992.

Extended European Search Report mailed Feb. 26, 2010, issued in European Patent Application No. 07811847.8, filed Apr. 13, 2007, 7 pages.

International Search Report mailed May 11, 2010, issued in International Application No. PCT/US2009/059589, filed Oct. 5, 2009, 10 pages.

International Search Report and Written Opinion mailed May 18, 2010, issued in International Application No. PCT/US2009/053050, filed Aug. 6, 2009, 15 pages.

International Search Report and Written Opinion mailed Oct. 26, 2010, issued in International Application No. PCT/US2010/026565, filed Mar. 8, 2010, 10 pages.

Cain, C.A., and S.-I. Umemura, "Concentric-Ring and Sector-Vortex Phased-Array Applicators for Ultrasound Hyperthermia," IEEE Transactions on Microwave Theory and Techniques 34(5):542-551, May 1986.

Chapelon, J.Y., et al., "The Feasibility of Tissue Ablation Using High Intensity Electronically Focused Ultrasound," Proceedings of the IEEE Ultrasonics Symposium 1993, Baltimore, Oct. 31-Nov. 3, 1993, pp. 1211-1214.

Chen, L., et al., "Effect of Blood Perfusion on the Ablation of Liver Parenchyma With High-Intensity Focused Ultrasound," Physics in Medicine and Biology 38(11):1661-1673, Nov. 1993.

Cheng, S.-Q., et al., "High-Intensity Focused Ultrasound in the Treatment of Experimental Liver Tumour," Journal of Cancer Research and Clinical Oncology 123(4):219-223, Apr. 1997.

Coad, J.E., "Thermal Fixation: A Central Outcome of Hyperthermic Therapies," Proceedings of the SPIE Conference on Thermal Treatment of Tissue: Energy Delivery and Assessment III 5698:15-22, San Jose, Calif., Jan. 23, 2005.

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):S13, May 1978.

Hallberg, L., et al., "Menstrual Blood Loss—A Population Study: Variation at Different Ages and Attempts to Define Normality," Acta Obstetricia et Gynecologica Scandinavica 45(3):320-351, 1966.

Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.

Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.

Orsini-Meinhard, K., "UW Tech-Transfer Program Putting Discoveries to Work," The Seattle Times, May 27, 2007, 8 pages.

Rabkin, B.A., et al., "Biological and Physical Mechanisms of HIFU-Induced Hyperecho in Ultrasound Images," Ultrasound in Medicine & Biology 32(11):1721-1729, Nov. 2006.

Sanghvi, N.T., et al., "High Intensity Focused Ultrasound (HIFU) for the Treatment of Rectal Tumors: A Feasibility Study," Proceedings of IEEE Ultrasonics Symposium 3:1895-1898, Cannes, France, Nov. 1-4, 1994.

"ThermoDox™ Animal Studies to be Presented at 6th International Symposium on Therapeutic Ultrasound in Oxford, England," Aug. 30-Sep. 2, 2006, Celsion, Inc., <http://www.celsion.com/news/releasedetail.cfm> [retrieved Oct. 8, 2007], 2 pages.

"ThermoDox™: Heat-Activated Liposome Drug," © 2007 Celsion, Inc., <http://www.celsion.com/products/ThermoDox.cfm> [retrieved Oct. 8, 2007], 3 pages.

Vaezy, S., et al., "Image-Guided Acoustic Therapy," Annual Review of Biomedical Engineering 3:375-390, Aug. 2001.

Winter, T.C., et al., "Focal Tumor Ablation: A New Era in Cancer Therapy," Ultrasound Quarterly 22(3):204-209, Sep. 2006.

Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.

Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5, Pt. 1):953-1081, May 1995.

International Search Report dated Jun. 26, 2009, in corresponding International Application No. PCT/US2008/082829, filed Nov. 7, 2008.

* cited by examiner

HEMOSTATIC SPARK EROSION TISSUE TUNNEL GENERATOR WITH INTEGRAL TREATMENT PROVIDING VARIABLE VOLUMETRIC NECROTIZATION OF TISSUE

BACKGROUND

Medical technology has made various attempts to treat internal pathologies such as uterine fibroid tumors, cervical neoplasia and HPV lesions, prostate hyperplasia or cancer, liver cancer, malignant bone and soft tissue sarcoma, and other tissue pathologies. In some instances, rigid needle systems have been devised for purposes of mechanically penetrating tissue and delivering treatment to the tissue. Such systems, however, are difficult to use, particularly when tortuous paths must be followed to reach the target tissue and when the tissue to be treated is resistant to entry of such needles. What is needed is a delivery system for a flexible catheter that can penetrate and destroy tissue masses or tumors of variable size and hardness.

SUMMARY

Described herein are various embodiments of an integrated multi-purpose catheter configured for insertion into tissue of a patient for treatment of the tissue. In at least one embodiment, the catheter comprises a radio frequency (RF) electrode and an insulating sleeve. The RF electrode has an elongated body configured to conduct electrical RF energy to a conductive tip at a distal end of the elongated body. The insulating sleeve surrounds the elongated body to suppress inadvertent shunting of RF energy from the elongated body when the catheter is being inserted into the patient's tissue.

In a first mode of operation for insertion of the catheter into the tissue of a patient, the conductive tip of the RF electrode is exposed outside the insulating sleeve. The RF electrode is configured to deliver, via the conductive tip, RF energy capable of producing sparks that erode the tissue of the patient and create a tunnel through which the catheter can advance into the tissue of the patient.

In a second mode of operation for treatment of the tissue in the patient, the insulating sleeve is retractable to expose a portion of the RF electrode between the conductive tip and the insulating sleeve. The RF electrode thereafter conducts non-sparking RF energy to the tissue in the patient. The non-sparking RF energy is able to heat the tissue surrounding the RF electrode to necrotize the tissue.

The insulating sleeve may be adjustably retracted to expose a desired portion of the RF electrode in accordance with a desired volume of tissue to be necrotized. Generally speaking, exposing a larger portion of the RF electrode will produce a greater volume of tissue destruction, while exposing a smaller portion of the RF electrode will produce a smaller volume of tissue destruction.

In combination with, or separate from, the features described above, the catheter may further comprise visualization apparatus that is operable to visualize the tissue surrounding the RF electrode. For example, in one embodiment, ultrasound imaging may be used. Visualization of the surrounding tissue can be used to determine the amount of the RF electrode to expose when retracting the insulating sleeve. Alternatively, or in addition, the visualization apparatus may be used to observe treatment-induced changes, such as bubbles, in the heated tissue to track the progression of treatment of the tissue.

In combination with, or separate from, the features described above, the catheter may further comprise a lumen configured to deliver a biocompatible electrically-resistant fluid that fills a volume around the RF electrode within the insulating sleeve when the catheter is in the first mode of operation.

Likewise, in combination with, or separate from, the features described above, the catheter may further comprise a lumen configured to deliver a biocompatible electrically-conductive fluid that perfuses the tissue surrounding the exposed portion of the RF electrode. The electrically-conductive fluid, such as a hypertonic saline or other electrolyte, increases the electrical conductivity of the tissue and enhances the volume of the tissue that is necrotized when RF heating energy is applied in the second mode of operation. Alternatively, or in addition, the biocompatible fluid may comprise a thermally-activated chemical adjuvant configured to aid in necrotizing the tissue with reduced thermal dosage. The lumen may also be a multi-purpose lumen configured to selectively deliver both a biocompatible electrically-resistant fluid, as referenced above, in the first mode of operation, and a biocompatible electrically-conductive fluid, as referenced above, in the second mode of operation.

In addition, the catheter may further include a second lumen that is configured to conduct fluid away from the tissue of the patient. In cooperation with the second lumen, a conveyance mechanism such as a pump, syringe, auger, etc., may be used to help draw the fluid (including, possibly, debris) away from the tissue.

In combination with, or separate from, the features described above, the catheter may further comprise a lumen configured to deliver a debriding agent that degrades the necrotized tissue.

In combination with, or separate from, the features described above, the catheter may further comprise a sleeve electrode disposed on the insulating sleeve. In the second mode of operation, the insulating sleeve is retractable to expose a portion of the RF electrode between the conductive tip and the sleeve electrode. The RF electrode is configured to conduct electrical RF energy to or from the sleeve electrode through the surrounding tissue in the patient. If desired, the sleeve electrode may be switchable to a non-conducting state in which the sleeve electrode is electrically isolated from RF energy conducted by the RF electrode. By switching the sleeve electrode into a non-conducting state, the catheter may operate in a monopolar mode of delivering RF energy.

Further, if desired, a plurality of sleeve electrodes may be disposed on the insulating sleeve. In such an embodiment, when the catheter is in the second mode of operation, each of the sleeve electrodes may be configured to separately and selectively switch between a conducting state and a non-conducting state. In the conducting state, a sleeve electrode is configured to conduct the RF energy to or from the RF electrode. In a non-conducting state, the sleeve electrode is electrically isolated from the flow of RF energy.

In combination with, or separate from, the features described above, the catheter may further comprise one or more temperature sensors that are configured to sense the temperature of the surrounding tissue to guide the delivery of the RF energy when the catheter is in the second mode of operation.

The present application also describes a method for inserting a catheter as described above into tissue of a patient for treatment. The method, in at least one embodiment, includes positioning the insulating sleeve to expose the conductive tip of the RF electrode; delivering first RF energy to the conductive tip in a first mode of operation for insertion of the catheter into the tissue of the patient, wherein the first RF energy produces sparks that erode the tissue of the patient and creates a tunnel through which the catheter advances into the tissue of the patient; and while in a second mode of operation for treatment of the tissue of the patient, retracting the insulating sleeve to expose a portion of the RF electrode between the conductive tip and the insulating sleeve, and conducting second RF energy from the RF electrode to the tissue in the patient, wherein the second RF energy heats the tissue surrounding the RF electrode for necrotization of the tissue without producing sparks.

As described above, the insulating sleeve may be adjustably retracted to expose a desired portion of the RF electrode in accordance with a desired volume of the tissue to be heated for necrotization. The tissue surrounding the RF electrode may be visualized to determine the amount that the insulating sleeve should be retracted. The method may also comprise visualizing the tissue surrounding the RF electrode to track the progression of treatment by observing treatment-induced changes in the heated tissue.

Furthermore, as described above, a biocompatible electrically-resistant fluid, a biocompatible electrically-conductive fluid, a thermally-activated chemical adjuvant and/or a debriding agent may be delivered to the catheter and/or to the tissue of the patient.

In combination with, or separate from, the method elements described above, the method may additionally comprise withdrawing the catheter from the tissue that was treated in the second mode of operation and repeating a delivery of RF energy via the conductive tip. In this instance, the RF energy is used to precipitate shrinkage of the patient's tissue and/or produce an area of coagulation that seals the tunnel in the treated tissue. In one aspect, this seal may act to prevent the flow of fluids, such as a chemical adjuvant or debriding agent, out of the tunnel. If desired, the catheter may thereafter be reinserted into a different location in the patient's tissue and the treatment repeated, which may be advantageous when treating large fibroids or tumors.

A catheter as described herein may also be combined with a rigid guide for directing the catheter into the tissue of a patient. The guide has a hollow core that is sized to receive the catheter and allow the catheter to extend therethrough. Visualization apparatus is used to obtain an image of the tissue of the patient, wherein, in the first mode of operation, the catheter is extendable from a distal end of the guide into the tissue of the patient. Using RF sparking energy, the catheter creates a tunnel in the tissue of the patient in a direction determined by the position of the guide. Thereafter the catheter uses RF heating energy to treat a volume of tissue surrounding the catheter.

It should be understood that the foregoing summary introduces only a selection of concepts in simplified form that are further described below in the Detailed Description. This summary is not intended to identify key features of the claimed subject matter, nor is it intended to be used to determine the scope of the claimed subject matter.

DESCRIPTION OF THE DRAWINGS

The foregoing aspects and many of the attendant advantages of this invention will become more readily appreciated as they become better understood by reference to the following detailed description, when taken in conjunction with the accompanying drawings, wherein.

DETAILED DESCRIPTION

As will be appreciated from the description herein, various implementations of a catheter can be used to penetrate tissue of a patient for treating various internal pathologies of the patient. Minimally-invasive surgery may thus be conducted in various parts of a patient's body.

In particular, the implementations described herein facilitate the insertion of a catheter through a cavity or tunnel that is created in the patient's tissue to reach intended target tissue for treatment. These implementations of a catheter can be applied to any part of the patient's body. As may be appropriate, the catheter may initially be inserted percutaneously, or alternatively the catheter may be transported through existing body orifices and cavities. Endoscopes, laparoscopes, transport catheters or probes can be employed to position the catheter near the tissue to be treated. For example, for treatment of a uterine fibroid, an implementation of a catheter as described herein may be transported transvaginally to a position in the vaginal or uterine cavity, after which the catheter is directed toward the tissue to be treated. For purposes of illustration, the implementations herein are shown and discussed in the context of using radio frequency (RF) energy for treatment of tissue in the patient, though other energy delivery systems, modalities, and therapies may be used to accomplish the desired treatment.

Figure 1:
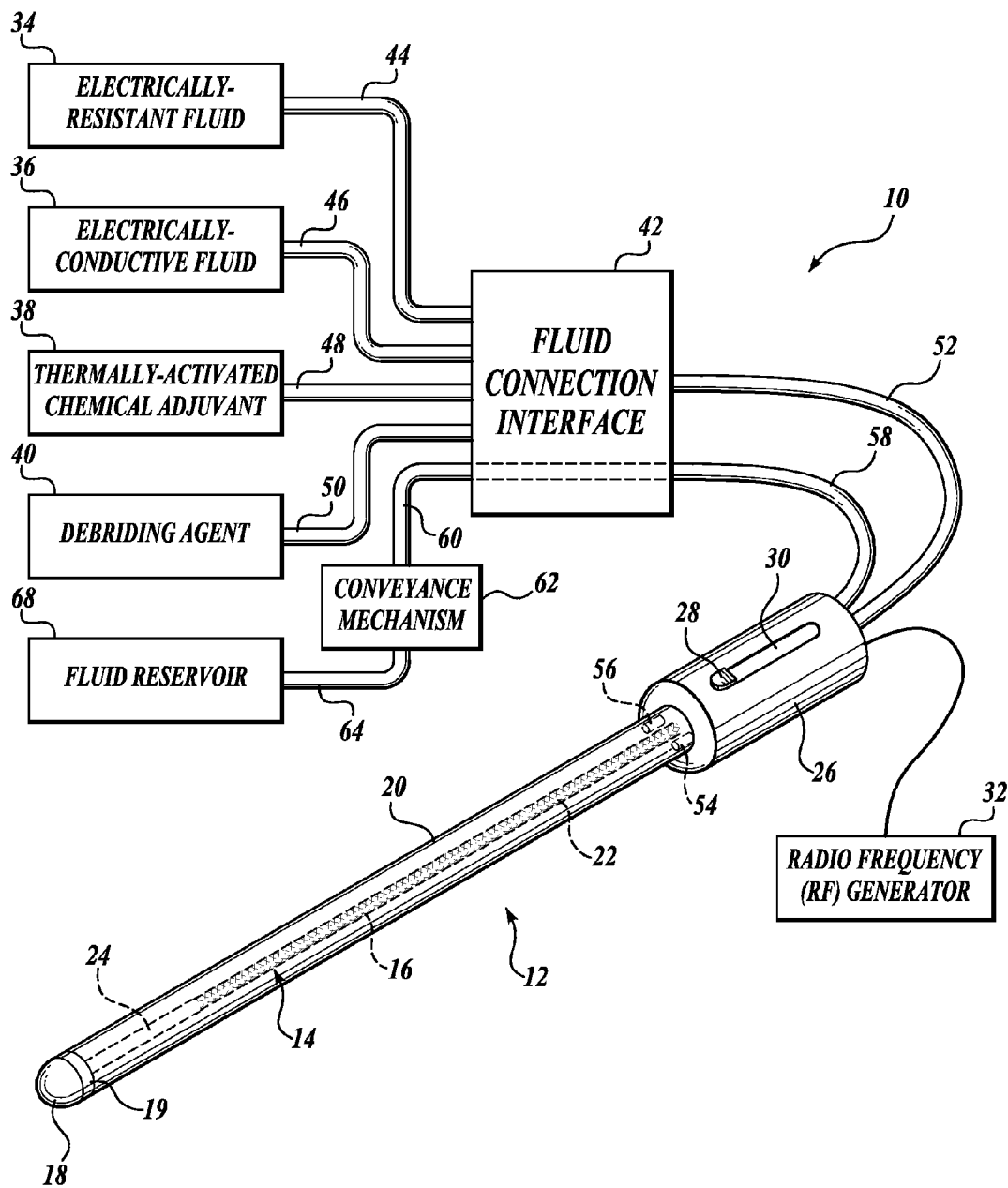
FIG. 1 illustrates one embodiment of a catheter system including a catheter constructed in accordance with principles of the present invention.

FIG. 1 illustrates one embodiment of a catheter system 10 that includes an implementation of a catheter 12 configured for insertion into tissue of a patient for treatment. The catheter 12 includes a radio frequency (RF) electrode 14 having an elongated body 16 and a conductive tip 18 at a distal end of the elongated body 16. As will be discussed in greater detail below, the elongated body 16 is configured to conduct electrical RF energy to the conductive tip 18, particularly when tunneling through the patient's tissue to reach intended target tissue for treatment. This particular embodiment further includes a ceramic insulator 19 in the form of a washer around the elongated body 16 and adjacent the conductive tip 18. The insulator 19 may be constructed of other insulative materials or may be omitted entirely, depending on the particular implementation of the catheter 12.

Surrounding the elongated body 16 is a hollow core insulating sleeve 20. The elongated body 16 extends axially through the interior of the insulating sleeve 20. The insulating sleeve 20 is configured to prevent electrical RF energy conducted by the elongated body 16 from being inadvertently transmitted by the elongated body 16 to the tissue of the patient surrounding the elongated body 16 when the catheter 12 is being inserted into the tissue of the patient. The dimensions of the insulating sleeve 20 may vary according to the particular implementation of the catheter 12, particularly in relation to the elongated body 16 of the RF electrode 14. For convenience of illustration, FIG. 1 depicts a volume of space separating the RF electrode 14 and the sleeve 20. In one or more actual implementations of the catheter 12, the volume of space may be much smaller or possibly larger if appropriate.

As further depicted in FIG. 1, a proximal end 22 of the elongated body 16 may be covered by an insulating material, such as, but not limited to, enamel, varnish, heat shrink tubing, etc. At the distal end of the elongated body 16, a portion 24 of the RF electrode 14 is not covered by the insulating material that covers the proximal end 22 of the RF electrode. In one embodiment, the distal portion 24 may measure 3-4 cm in length, for example, depending on the particular form of the RF electrode 14 that is being used. Unlike the insulating material covering the proximal end 22 of the RF electrode 14, which is fixed relative to the RF electrode, the insulating sleeve 20 is retractable to expose some or all of the portion 24 of the RF electrode 14 to tissue of the patient.

In an embodiment as depicted in FIG. 1, the catheter 12 may include a handle 26 that includes a retracting mechanism 28 connected to the insulating sleeve 20. In this particular configuration, the retracting mechanism 28 is mechanically connected to the insulating sleeve 20 such that, as the retracting mechanism 28 is drawn back through a groove 30 in the handle, the insulating sleeve 20 is drawn inward into the interior of the handle 26, thus exposing the portion 24 of the RF electrode 14 at the distal end of the electrode. See, for example, FIGS. 3, 4B, 5B, 6, 7A, and 7B, as well as FIGS. 8C and 9. Markings adjacent to the groove 30 may be used to monitor the distance that the insulating sleeve 20 has been retracted. Of course, persons of ordinary skill in the art will readily recognize other suitable mechanisms that may be used for retracting the insulating sleeve 20, which may include other controls such as dials, motors, pull wires, etc. As described herein, exposing the distal portion 24 of the RF electrode 14 allows for a variable volumetric destruction of tissue in the patient by delivering RF heating energy through a variable volume of tissue surrounding the distal end of the RF electrode 14. Such RF energy may be generated by a radio frequency (RF) signal generator 32 as shown in FIG. 1.

The catheter 12 is configured to operate in different modes of operation. In a preferred embodiment as described herein, the catheter 12 is configured to operate in a first mode and second mode of operation. Prior to discussing the different modes of operation of the catheter 12, it is helpful to first observe other features that may be included in the catheter system 10 as shown in FIG. 1. Along with delivering RF energy, the catheter 12 may be configured to deliver various fluids depending on the particular mode of operation of the catheter 12 and the status of the treatment being provided to the patient.

As indicated in FIG. 1, the catheter system 10 may include a source of electrically-resistant fluid 34, a source of electrically-conductive fluid 36, a source of a thermally-activated chemical adjuvant 38, and a source of a debriding agent 40. Each of these fluid sources is shown connected to a fluid connection interface 42 via respective tubes 44, 46, 48, and 50. As will be appreciated from the description herein, the fluid connection interface 42 may be configured to cause any one or combination of the fluids to be delivered from the sources 34, 36, 38, or 40, to a tube 52 that leads to the catheter 12. The fluid or fluids conveyed by the tube 52 are communicated through the handle 26 to a first lumen 54 that delivers the fluid(s) to the interior of the catheter 12. In a first mode of operation where the insulating sleeve 20 is fully extended to the tip 18 of the catheter 12, fluid delivered via the lumen 54 is contained within the insulating sleeve 20 and fills the volume around the RF electrode 14. See, e.g., FIGS. 4A and 5A. In a second mode of operation where the insulating sleeve 20 is retracted to expose a portion 24 of the RF electrode 14, the fluid delivered via the lumen 54 may flow outward from the catheter 12 and perfuse the tissue of the patient surrounding the exposed portion 24 of the RF electrode 14. See, e.g., FIGS. 4B and 5B.

During either the first or second mode of operation of the catheter 12, a return channel may be used to convey fluid away from the tissue of the patient. For that purpose, the embodiment shown in FIG. 1 further includes a second lumen 56. The second lumen 56 may be connected through the handle 26 to a return tube 58 connected to the fluid connection interface 42. In the embodiment shown, the return tube 58 is directly connected through the fluid connection interface 42 to a tube 60 that is coupled to a conveyance mechanism 62. A further tube 64 couples the conveyance mechanism 62 to a fluid reservoir 68 that receives and collects the return fluid flowing from the catheter 12.

The conveyance mechanism 62 is an optional feature, as are the fluid sources illustrated in FIG. 1. The conveyance mechanism 62 is shown in block form as it is intended to represent a wide variety of mechanisms that may be used to enhance the flow of fluids from the catheter 12. In at least one embodiment, the conveyance mechanism 62 may comprise a pump that applies a negative fluid pressure to the tubes 60 and 58, thus drawing fluids from the catheter 12 through the second lumen 56. In another embodiment, the conveyance mechanism 62 may comprise a stopcock and syringe that is operable to draw fluids back through the tubes 60 and 58. In this embodiment, the syringe may also comprise the fluid reservoir 68. In yet another embodiment, the conveyance mechanism 62 may comprise an auger or screw-shaped element. The auger or screw may extend axially through the tubes 60 and 58 and through the second lumen 56 into the catheter 12. By virtue of rotating the auger or screw, fluids as well as other debris may be drawn through the second lumen 56 and ultimately to the fluid reservoir 68. An auger or screw-shaped element of this type is particularly useful when the fluid being drawn from the catheter 12 further includes debris, such as necrotized tissue of the patient. Additionally, gases produced in the vicinity of the catheter 12 may be drawn through the second lumen 56 and the tubes 58, 60, 64 to the fluid reservoir 68. Where suction pressure to draw fluids from outside the catheter 12 is desired during the first operating mode, one or more ports (not shown) connected to the second lumen 56 may be provided on the outside of insulating sleeve 20.

It should be recognized that FIG. 1 illustrates only one embodiment of a catheter 12 that can be used to achieve various benefits of the present invention. Alternative or additional forms and features may be incorporated into other embodiments of the catheter 12, as will be seen in the figures and description that follow. The scope of the invention should therefore not be limited to the precise form of the embodiment shown in FIG. 1.

The catheter 12 is configured to use an electrical discharge from the tip 18 for ablating tissue of the patient to create a cavity or tunnel in the tissue through which the catheter 12 can advance into the tissue of the patient. By using an electrical discharge at a radio frequency, hazards from electric shock are minimized since radio frequency is above the neuromuscular threshold for reacting to such electrical discharge. Furthermore, by delivering RF energy at a magnitude that produces electric sparks, one is able to hemostatically ablate and penetrate hard or soft tissue at the tip 18 of the electrode 14. Provided that the tissue of the patient is electrically conductive and contains volatile elements such as water, the RF sparking energy causes a rapid and explosive expansion of water vapor bubbles, for example, when the RF sparks enter the tissue and cause heating at a microscopic level. Small pockets of steam in the intracellular or interstitial fluids cause rupture of the cells, thus permitting the electrode 14 to advance with greater ease into the tissue of the patient.

Figure 2A:
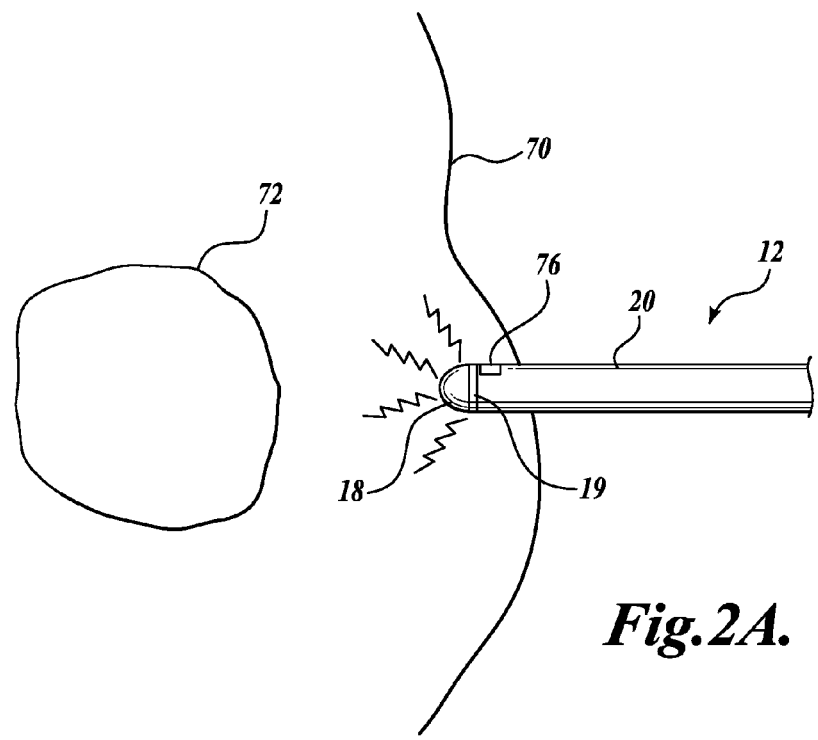
FIGS. 2A and 2B illustrate a first mode of operation of the catheter for insertion of the catheter into tissue of the patient using RF sparking energy.

FIG. 2A illustrates a first mode of operation of the catheter 12 for insertion of the catheter 12 into tissue 70 of the patient. As shown, the conductive tip 18 of the RF electrode is exposed outside of the insulating sleeve 20. The RF electrode 14 is configured to deliver, via the conductive tip 18, first RF energy that is capable of producing sparks which erode the tissue 70 of the patient and create a tunnel through which the catheter 12 can advance into the tissue 70 of the patient. As further illustrated in FIG. 2A, the catheter 12 is shown tunneling toward a tissue mass 72 identified, in this example, as a tumor.

Figure 2B:
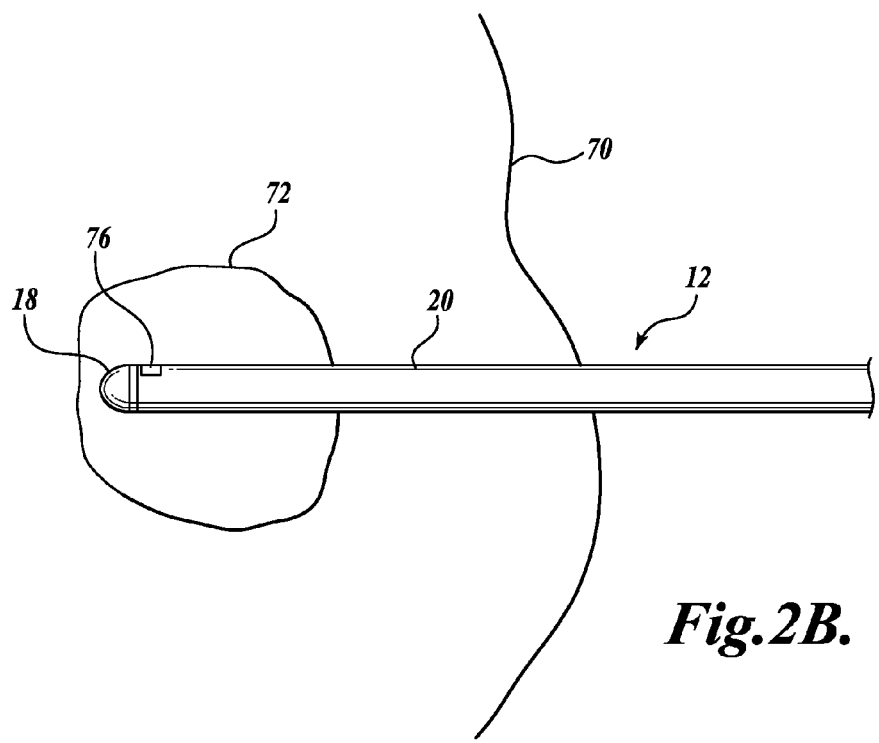
Figure 8A:
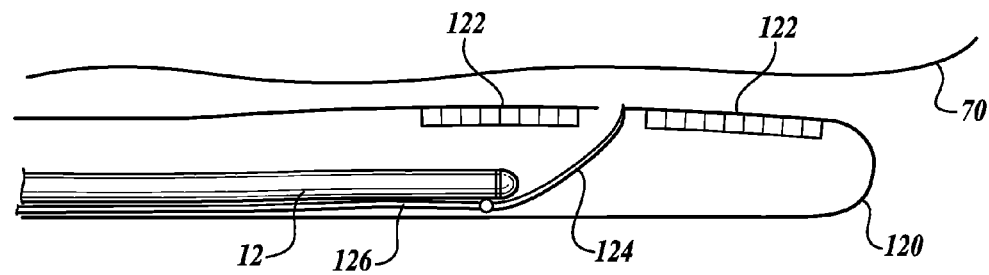
FIGS. 8A and 8B illustrate an ultrasound probe transporting a catheter of FIG. 1, wherein a deflection mechanism is selectively positioned to guide the trajectory of the catheter in the first mode of operation when the catheter is tunneling into the tissue of the patient.
Figure 8B:
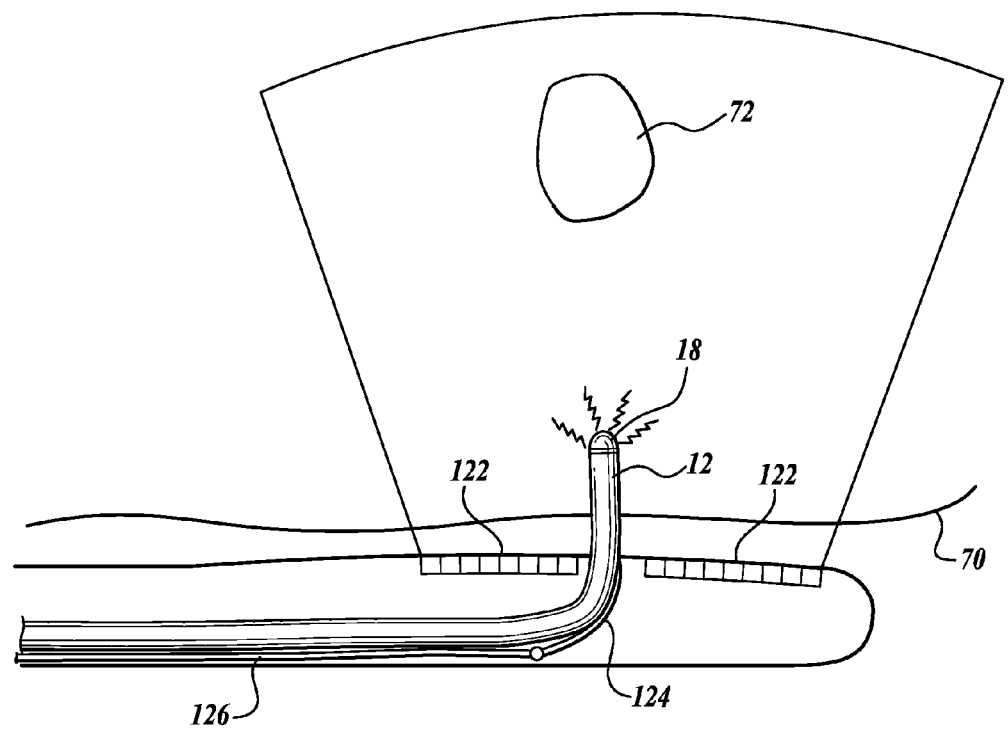
Figure 8C:
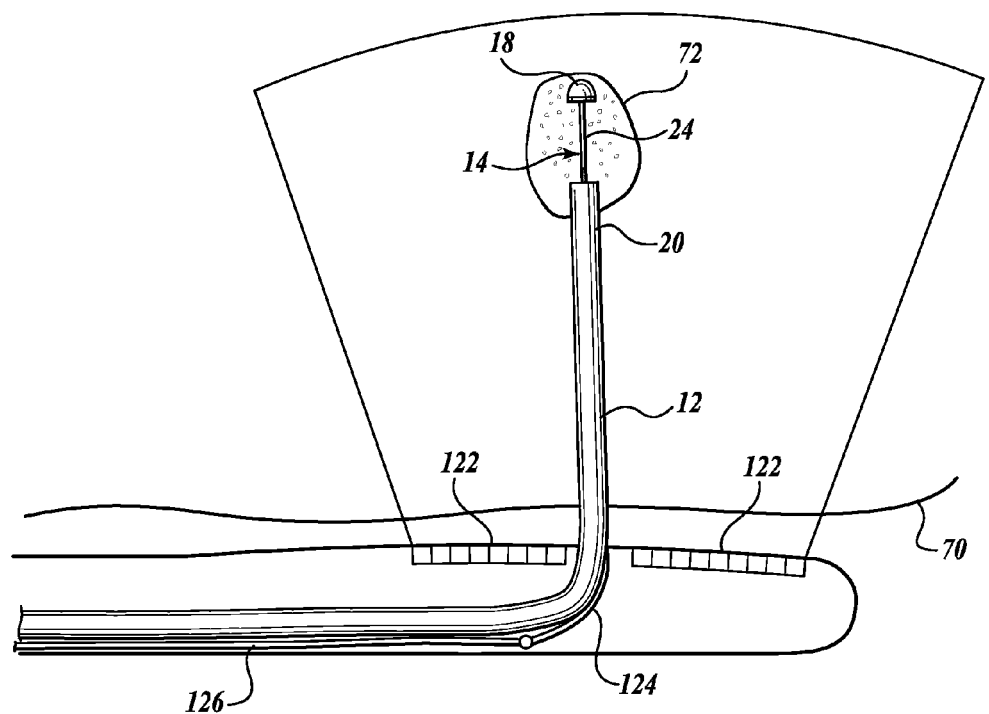
FIG. 8C illustrates the catheter of FIGS. 8A and 8B in the second mode of operation where the ultrasound array of the probe is used to observe bubbles or vacuoles induced by the RF heating energy in the tissue being treated.

Proceeding to FIG. 2B, the catheter 12 is shown having penetrated the tissue 70 of the patient as well as the tumor 72. The length of the tunnel through which the catheter 12 is inserted is typically determined by the length of time that the RF spark discharge and forward forces are applied to the catheter 12. Typically, the tunnel extends nearly to the distal-most boundary of the tumor mass 72. Where appropriate, mechanical stops may be configured or programmed to prevent the catheter 12 from advancing farther than intended. This may avoid unwanted tissue penetration and tunneling of healthy tissue beyond the target tissue to be treated. External or internal gauges on the catheter 12 can help determine the distance that the catheter 12 has been inserted into the patient. Alternatively or in addition, ultrasonic imaging such as illustrated in FIGS. 8A-8C, may also be used to track the distance that the catheter 12 has been inserted into the tissue of the patient.

The sparking discharge illustrated in FIG. 2A is accomplished using monopolar delivery of RF sparking energy to the tissue 70. For monopolar delivery, a ground plate is positioned elsewhere on the patient in conductive connection with the skin of the patient. When RF sparking energy is applied, the eroding forces of the sparking discharge are most pronounced in the area concentrated around the tip 18 of the RF electrode. As the RF energy continues in various paths from the tip 18 through the body of the patient, the eroding force of the RF energy is quickly attenuated and thus does not damage tissue of the patient outside the immediate area of the tip electrode 18.

In this mode of operation, the insulating sleeve 20 is positioned adjacent the ceramic insulator 19 to insulate the elongated body 16 of the RF electrode 14 from the tissue of the patient. This minimizes any unintended leakage or shunting of RF energy from the elongated body 16 to the adjacent tissue of the patient. The RF sparking energy is thus concentrated at the tip 18 of the electrode 14.

Once the catheter 12 has tunneled through the tissue of the patient to the desired position in the tumor mass 72, the delivery of the RF sparking energy is terminated. The catheter 12 thereafter proceeds to a second mode of operation for treatment of the tumor mass 72 in the patient.

Figure 3:
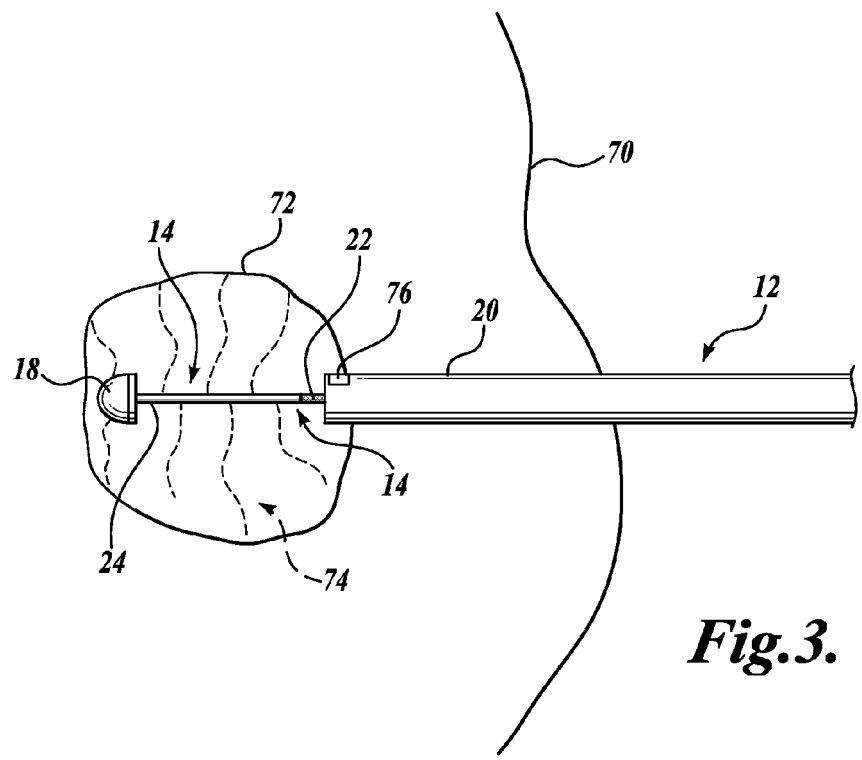
FIG. 3 illustrates a second mode of operation of the catheter in which an insulating sleeve has been retracted to expose a portion of the RF electrode for monopolar delivery of RF heating energy.

In the second mode of operation, the insulating sleeve 20 is retracted to expose a portion 24 of the RF electrode 14 between the conductive tip 18 and the insulating sleeve 20, as illustrated in FIG. 3. The RF electrode 14 is configured to conduct second RF energy to the tissue of the tumor mass 72 in the patient. The second RF energy is capable of heating the tissue 72 surrounding the RF electrode 14 for necrotization of the tissue without producing sparks. By using sparkless discharge of RF energy in the second mode of operation, heating of the surrounding tissue can lead to necrosis of a larger volume of tissue, typically after the temperature of the tissue has been raised above 45° C. A temperature sensor 76 may be positioned on the catheter 12 to monitor the temperature of the adjacent surrounding tissue. Monitoring the temperature may help guide the delivery of the RF heating energy for treatment. The sensor 76 may be a low-profile commercially-available temperature sensor affixed to the outside of the insulating sleeve 20. One or more additional temperature sensors could be added in alternate locations as appropriate to monitor the rise in temperature of surrounding tissue.

Persons having ordinary skill in electrode design will recognize that various materials, including memory metals, may be used to construct the RF electrode 14. One example of a surgical-grade material that is suitable for constructing the RF electrode is nitinol. Nitinol is a super-elastic memory alloy well known for its ability to bend around tight corners, yet retain its original form without fatigue or metallic yield.

Figure 5A:
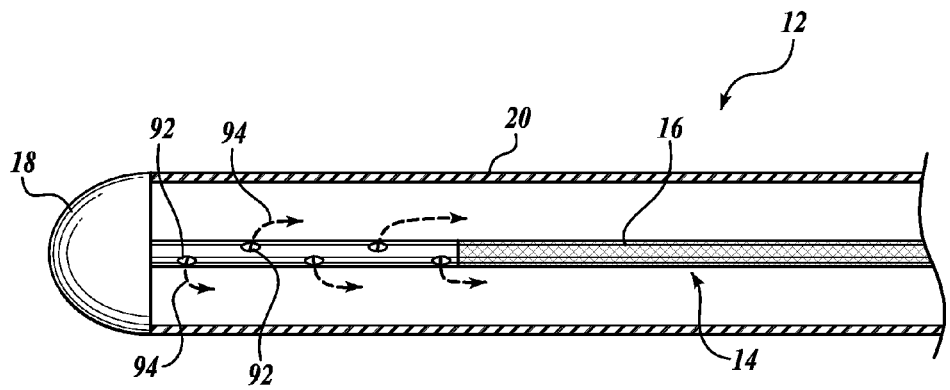
FIGS. 5A and 5B illustrate another alternative embodiment of the catheter of FIG. 1.
Figure 5B:
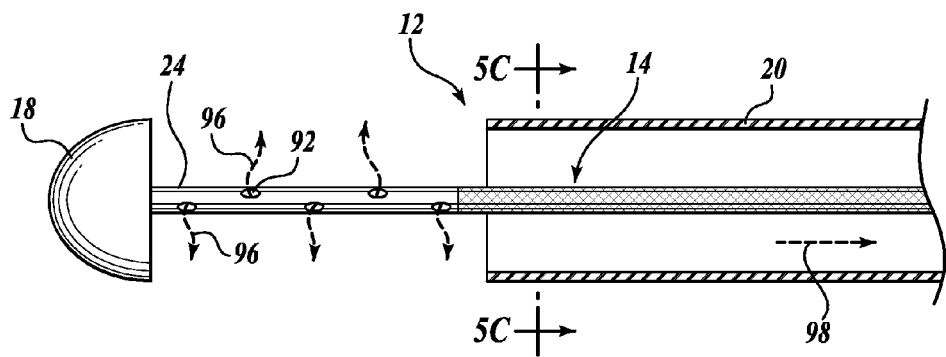

In some cases, the conductive tip 18 and/or the body 16 of the RF electrode 14 may be coated with known materials or etched with known patterns to more easily observe the position of the RF electrode 14 in the patient via enhanced radioopacity or ultrasonic echogenicity, respectively. The tip 18 may be comprised of a thermally refractory metal alloy, such as platinum-iridium, for example, to reduce the erosion of the metal surface of the tip 18 when RF energy is delivered via the tip. At present, it is anticipated that the elongated body 16 of the RF electrode 14 may measure (in diameter) in the range of 0.004 to 0.060 inches in diameter. For example, an embodiment of the RF electrode 14 may be made of nitinol having an outside diameter in the range of 0.010 inches in order to have adequate flexibility to turn corners, such as at a launch point as shown in FIG. 8B. Larger diameter electrode may be used in other embodiments, particularly if a coiled or braided configuration is used for the RF electrode 14, or alternatively if a hollow core conductor is used for the RF electrode 14 as shown in FIGS. 5A and 5B. In some aspects, larger diameter conductors offer better surface area for delivery of RF energy, as provided in the second mode of operation of the catheter 12.

FIG. 3 illustrates a monopolar delivery of the second RF energy, as illustrated pictorially by dashed lines 74. As previously discussed, when delivering RF energy in a monopolar mode to the patient, the RF energy follows various paths through the patient toward a patient plate positioned elsewhere in conductive connection to the patient. The density of the RF energy in the patient's tissue 72 is most concentrated near the RF electrode 14. Beyond the first few centimeters from the RF electrode 14, the density of the RF energy quickly decreases, thus leading to a decrease of the tissue heating caused by the RF energy. Because of this steep temperature gradient, the heating of the tissue 72 is generally confined to the volume of tissue surrounding the RF electrode 14.

After sufficient RF energy has been delivered to the tissue 72 to achieve the desired heating and necrotization of the tissue, the delivery of the second RF energy may be terminated, after which the catheter 12 may be withdrawn from the tissue of the patient. Normal body processes that break down the necrotized tissue, including the action of microphages, will eventually cause the necrotic tissue 72 to be eliminated and/or absorbed.

During the first mode of operation of the catheter 12 as illustrated in FIG. 2A, where a spark discharge is delivered from the conductive tip 18 and forward pressure is applied to the catheter 12, one or more non-conducting fluids may be delivered to the interior of the catheter 12 to help suppress leakage of electrical current from the elongated body 16 of the RF electrode 14. Inadvertent leakage or shunting of current from the elongated body 16 might reduce the effectiveness of the sparking energy at the tip 18. As depicted in FIG. 1, the first lumen 54 may be configured to deliver a biocompatible electrically-resistant fluid from the fluid source 34 to fill the volume within the insulating sleeve 20 around the RF electrode 14. Suppressing leakage current from the unexposed RF electrode 14 also prevents unintended damage to the tissue adjacent the elongated body 16 while the RF electrode 14 is tunneling into the tissue of the patient. Examples of electrically-resistant or non-conducting fluids that may be used in connection with the catheter 12 include such media as glycine, a sucrose or dextrose solution, sorbitol or mannitol.

After the catheter 12 has tunneled to a desired position in the patient, as shown in FIG. 2B, and the delivery of RF sparking energy has ceased, the electrically-resistant fluid within the catheter 12 may be evacuated using the second lumen 56 illustrated in FIG. 1 and deposited in the fluid reservoir 68. In one embodiment, a pump may be used to draw the electrically-resistant fluid out of the catheter 12. In another embodiment, a stopcock and syringe arrangement may be used to evacuate the electrically-resistant fluid. Alternatively, or in addition, another fluid, such as an electrically-conductive saline, may be used to flush out the electrically-resistant fluid.

Figure 4A:
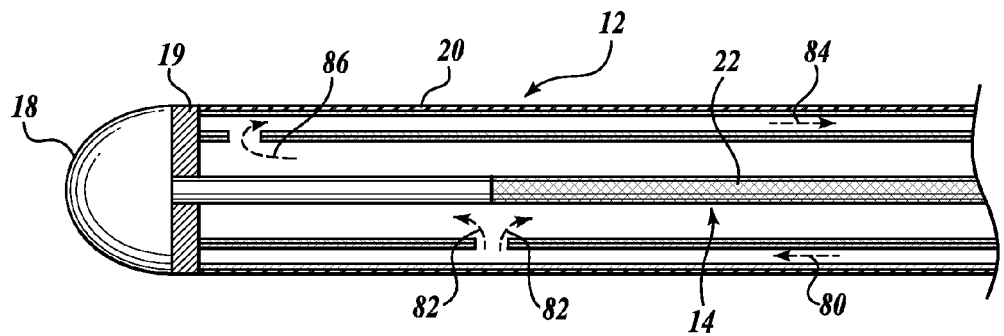
FIGS. 4A and 4B illustrate an alternative embodiment of the catheter of FIG. 1.

The first lumen 54 and the second lumen 56 depicted in FIG. 1 represent only one possible embodiment in which lumens are configured to conduct fluid to and from the catheter 12. FIG. 4A illustrates an alternative embodiment of a catheter 12. In this embodiment, the catheter 12 has a conductive tip 18 and an insulating sleeve 20 much like the embodiment shown in FIG. 1. In FIG. 4A, the catheter 12 is shown in the first mode of operation where the insulating sleeve 12 is extended such that it directly abuts the ceramic insulator 19 adjacent to the conductive tip 18. A first lumen 80 is configured along the interior of the insulating sleeve 20, as shown in the cross section view in FIG. 4C. An open port in the side of the lumen 80 allows fluid flowing through the first lumen 80 to fill the interior of the catheter 12, as illustrated by arrows 82.

Figure 4B:
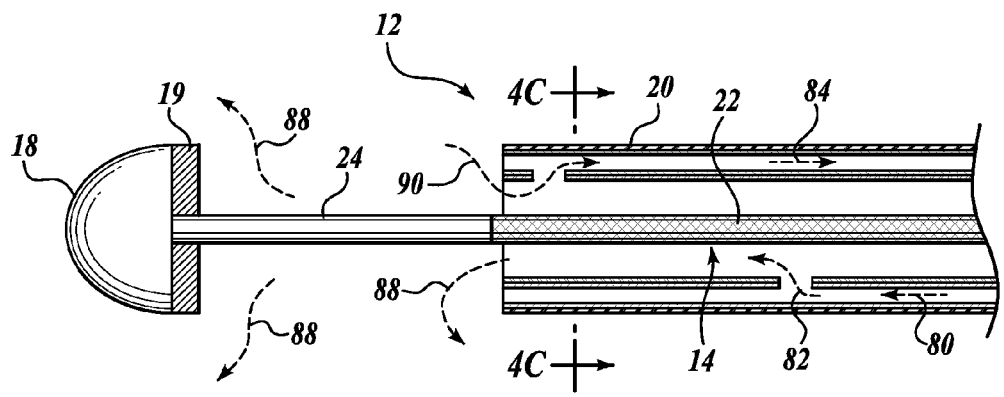
Figure 4C:
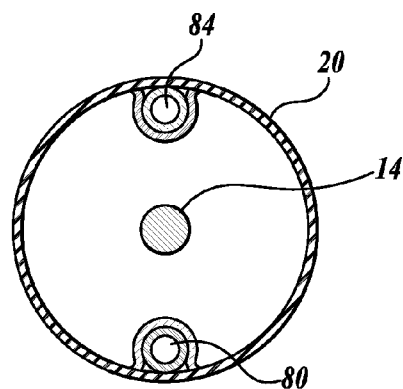
FIG. 4C illustrates a cross section of the embodiment shown in FIG. 4B.

The embodiment in FIG. 4A further illustrates a second lumen 84 defined inside the insulating sleeve 20, as shown in cross section in FIG. 4C, for conducting fluid away from the catheter 12. An open port in the side of the second lumen 84 allows fluid within the interior of the catheter 12 to enter the lumen 84 as illustrated by arrow 86. A conveyance mechanism 62 as shown in FIG. 1 may be used to help draw fluids through the second lumen 84 away from the catheter 12 to the fluid reservoir 68.

FIG. 4B illustrates the embodiment of the catheter 12 shown in FIG. 4A, except in FIG. 4B, the catheter 12 is in the second mode of operation. Accordingly, the insulating sleeve 20 has been retracted to expose a portion 24 of the RF electrode 14 between the conductive tip 18 and the insulating sleeve 20. A fluid flowing through the first lumen 80 is capable of exiting the lumen 80 through the open port as illustrated by the arrow 82.

To help increase the size of the thermal lesion in the patient's tissue 72 (e.g., as illustrated in FIG. 3), a lumen in the catheter 12 may be configured to deliver a biocompatible electrically-conductive fluid to the tissue 72. The fluid perfuses the tissue surrounding the exposed portion 24 of the RF electrode 14 to increase the electrical conductivity of the tissue and thereby enhance the volume of the tissue that is heated and ultimately necrotized. With respect to the embodiment shown in FIG. 4B, an electrically-conductive fluid, such as a hypertonic saline or concentrated electrolyte, which may include Ringer's solution, is delivered through the first lumen 80 to the interior of the catheter 12. Where the insulating sleeve 20 has been retracted, the conductive fluid flows outward into the surrounding tissue as illustrated by arrows 88. This administration of a biocompatible electrically-conductive fluid improves the range of tissue through which the RF heating energy may flow and expands the zone of tissue that reaches the threshold temperature for necrotization. One or more temperature sensors (e.g., as shown in FIGS. 2A, 2B, and 3) may be positioned on the catheter 12 to monitor the temperature of the adjacent tissue, which may help guide the delivery of the RF heating energy for treatment. For example, a low-profile commercially-available temperature sensor affixed to the outside of the insulating sleeve may report when the tissue adjacent to the catheter 12 has reached a necrotizing temperature.

If desired, the catheter 12 may be configured to conduct fluid away from the tissue surrounding the RF electrode 14 through the second lumen 84, as illustrated in FIG. 4B. Such fluid may flow, according to arrow 90, into an open port of the second lumen 84 and be conducted away from the tissue to the fluid reservoir 68 shown in FIG. 1. The fluid drawn through the second lumen 84 may include the electrically-conductive fluid delivered by the first lumen 80, as well as other fluids including intracellular fluids from the tissue that is broken down in the process of heating the tissue. Gases and tissue debris may also be drawn with the fluid through the second lumen 84. As noted earlier, a conveyance mechanism 62, such as an auger or screw that extends axially into the second lumen 84, may assist in conducting the fluids and debris away from the catheter 12.

FIGS. 5A and 5B illustrate another alternative embodiment of a catheter 12 that may be used in treating tumor masses or other tissue pathologies in a patient. As with the catheter 12 shown in FIGS. 4A and 4B, the catheter 12 in FIGS. 5A and 5B includes an insulating sleeve 20 that surrounds the elongated body 16 of an RF electrode 14. During the first mode of operation for insertion of the catheter 12 into the tissue of the patient, the insulating sleeve 20 is in an extended position where it abuts the conductive tip 18. The RF electrode 14 conveys RF sparking energy to the conductive tip 18 which enables the catheter to penetrate the tissue and tunnel through the tissue to be treated. In contrast to the embodiment shown in FIGS. 4A and 4B, the embodiment in FIGS. 5A and 5B does not include a ceramic insulator 19.

Figure 5C:
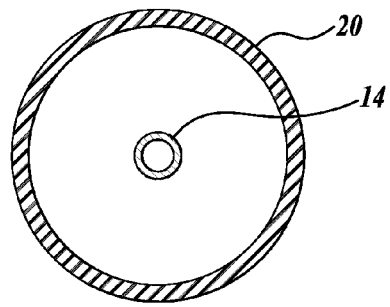
FIG. 5C illustrates a cross section of the embodiment shown in FIG. 5B.

As further depicted in FIGS. 5A and 5B, as well as in the cross section shown in FIG. 5C, a hollow channel within the RF electrode 14 provides a first lumen capable of delivering fluid to the catheter 12. During the first mode of operation, as shown in FIG. 5A, a biocompatible electrically-resistant fluid may flow through the RF electrode 14 and exit through open ports 92 into the interior of the insulating sleeve 20, as depicted by the arrows 94. The non-conducting fluid fills the volume around the RF electrode 14 within the insulating sleeve 20 and insulates the elongated body 16 when the catheter 12 is tunneling into the patient's tissue.

In the second mode of operation for treatment of tissue in the patient, as illustrated in FIG. 5B, the insulating sleeve 20 is retracted to expose a portion 24 of the RF electrode between the conductive tip 18 and the insulating sleeve 20. Fluid flowing through the RF electrode 14 may exit the ports 92 and, as depicted by the arrows 96, flow into the adjacent tissue to be treated. As previously described, in the second mode of operation, it may be advantageous to perfuse a concentrated saline or electrolyte into the surrounding tissue to enhance the electrical conductivity of the tissue and thus enhance production of a thermal lesion in the tissue.

In both FIGS. 5A and 5B, the insulating sleeve 20 may further be configured to act as a second lumen through which fluid may be conducted away from the tissue of the patient. A conveyance mechanism 62, as shown in FIG. 1, may be connected to the interior of the insulating sleeve 20 to draw fluid back toward the fluid reservoir 68, as indicated by arrow 98. This process of drawing fluid away from the catheter 12 may be conducted during either the first or second mode of operation, and may further conduct gases and debris away from the tissue being subjected to the RF energy.

As may be appreciated from the foregoing description, a multi-purpose lumen may be configured to deliver the electrically-resistive fluid 34 as well as the electrically-conductive fluid 36 to the catheter 12. The multi-purpose lumen may also be configured to conduct other types of fluid. For example, during or after the period in which the tissue of the patient is necrotized in the second mode of operation, the multi-purpose lumen may be configured to deliver a debriding agent from the source 40 shown in FIG. 1. Chemical debriding agents can assist in breaking down and dissipating necrotic tissue that results from the RF heating caused by the electrode 14. Chemical debridement typically employs enzymes or other compounds to dissolve necrotic tissue and is typically more selective than mechanical debridement. One example of an exogenous debriding enzyme is a bacterial collagenase from *Clostridium histolyticum*. Additional non-limiting examples of debriding enzymes include fibrinolysin, DNAse, and papain.

In yet another embodiment, a thermally-activated chemical adjuvant may be delivered separately or in connection with delivery of the electrically-conductive fluid that perfuses the tissue surrounding the RF electrode in the second mode of operation. A thermally-activated chemical adjuvant is configured to aid in necrotizing the tissue with reduced thermal dosage. For example, heat-sensitive liposomes or other heat-sensitive blood-borne vehicles may thus be used to deliver therapeutic agents of various types, e.g., antitumor agents, cytotoxic drugs, debriding enzymes, and/or wound-healing stimulants, when hyperthermia-inducing energy is applied to the target tissue. One example of a commercially-available, heat-activated liposome is available under the name Thermo-Dox from Celsion Corporation of Columbia, Md. Heat-sensitive liposomes may also be configured to carry proteins that either digest the necrotized tissue or induce the body's own immune response. The liposomes are prepared to release the proteins when a threshold temperature in the tissue is reached. This threshold temperature may be lower than the temperature required for destruction of the tissue by heating alone.

In some circumstances, to ensure the thermally-activated chemical adjuvant reaches the tissue to be treated, it may be appropriate to inject the chemical adjuvant into the patient's bloodstream which is circulated throughout the body. Alternatively, the thermally-activated chemical adjuvant may be injected directly into the targeted tissue. An implementation of a catheter 12 may include one or more needles that can be extended from the catheter during or after the RF tunneling is completed. The needles are preferably configured to deliver the thermally-activated chemical adjuvant to the tissue to be treated prior to delivery of the RF heating energy. Lower temperature treatment is advantageous in that it creates less thermally-fixed tissue which the body may not be able to reabsorb, and thus allows greater shrinkage of the treated tissue 72 post treatment.

Figure 6:
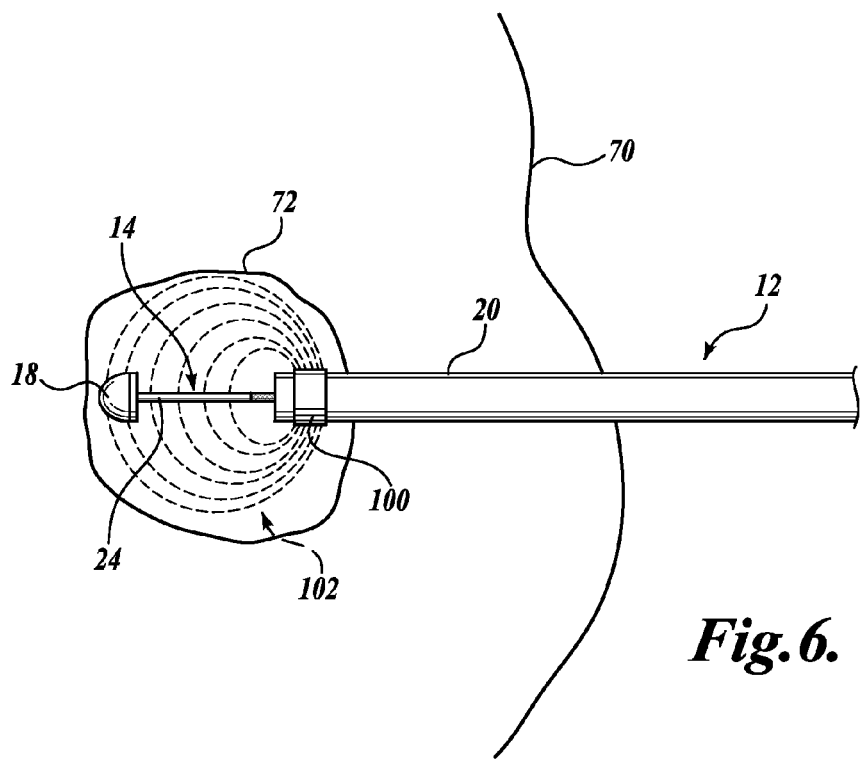
FIG. 6 illustrates a second mode of operation of the catheter in which the insulating sleeve has a sleeve electrode for bipolar delivery of RF heating energy.

FIG. 6 illustrates yet another embodiment of a catheter 12 that may be used to tunnel through tissue of a patient and treat a volume of tissue in the patient through heat-inducing RF energy. In contrast to the monopolar delivery of RF heating energy as shown in FIG. 3, FIG. 6 illustrates a bipolar delivery of RF energy to treat the tissue mass 72 of the patient. The catheter 12 includes a sleeve electrode 100 disposed on the insulating sleeve 20. In combination with the RF electrode 14, the sleeve electrode 100 provides an electrical path for RF energy to be conducted through the tissue 72. As depicted in FIG. 6, electric flux lines 102 extend between the RF electrode 14 and the sleeve electrode 100, representing appropriately the flow of electrical current. The sleeve electrode 100 may be electrically coupled through the catheter 12 to a radio frequency (RF) generator 32 as shown in FIG. 1 or to ground. Thus, in the second mode of operation, the RF electrode 14 is able to conduct the RF heating energy to or from the sleeve electrode 100 through the tissue 72 in the patient.

The RF generator 32 may be a dual-purpose generator configured to switchably deliver to the RF electrode 14 said first RF energy that is capable of producing sparks to erode the tissue near the tip 18 of the RF electrode and said second RF energy that is capable of heating the tissue surrounding the RF electrode 14 without producing sparks.

The embodiment shown in FIG. 6 may also be configured to operate alternately between a monopolar mode and bipolar mode for delivering RF energy through the tissue 72 of the patient. In a monopolar mode, the sleeve electrode 100 is electrically isolated from the flow of RF energy, thus causing RF energy from the RF electrode 14 to conduct through the patient toward a conductive plate placed elsewhere on the patient. In a bipolar mode, the sleeve electrode is electrically connected to the flow of RF energy and conducts the RF heating energy to or from the RF electrode 14 through the tissue 72 in the patient. The sleeve electrode 100 is switchable between conducting RF energy in the bipolar mode of operation and being electrically isolated in the monopolar mode of operation.

Figure 7A:
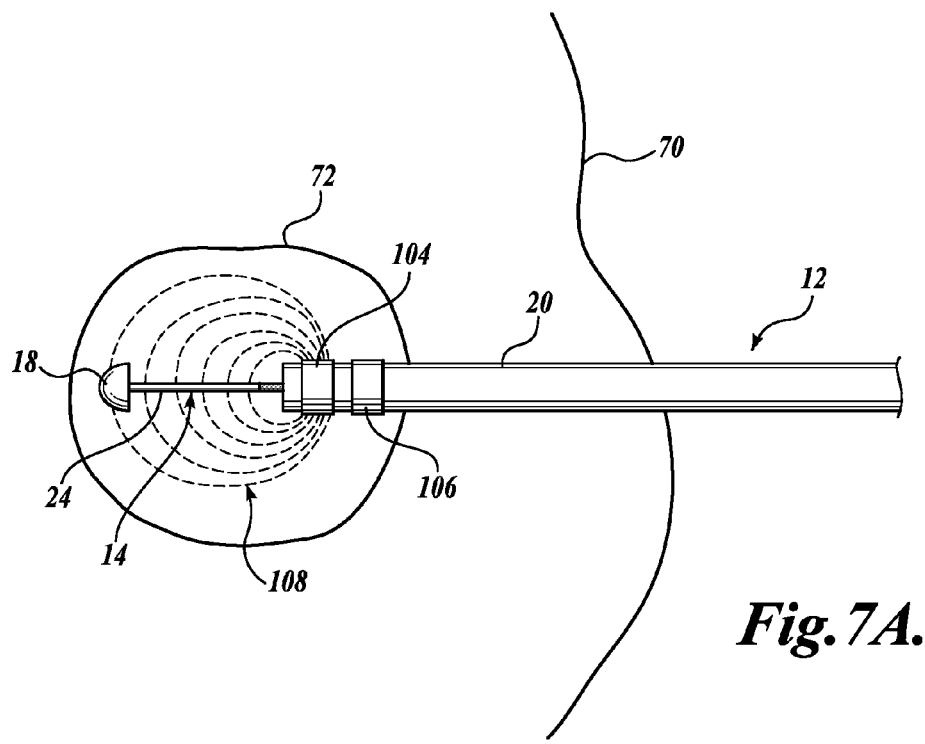
FIGS. 7A and 7B illustrate a second mode of operation of the catheter in which the insulating sleeve has a plurality of sleeve electrodes for bipolar delivery of RF heating energy.
Figure 7B:
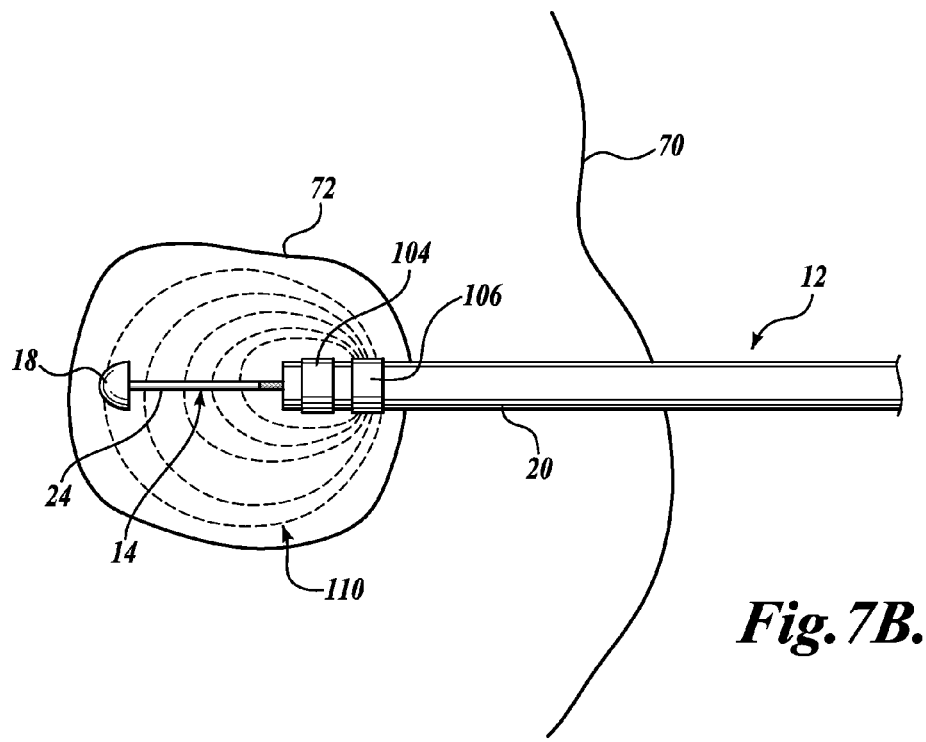

In still another embodiment, the catheter 12 may include a plurality of sleeve electrodes 104, 106 disposed on the insulating sleeve 20, as depicted in FIGS. 7A and 7B. Like the sleeve electrode 100 described above, the sleeve electrodes 104, 106 may be electrically coupled through the catheter 12 to the radio frequency (RF) generator 32 shown in FIG. 1 or to ground. In this particular embodiment, when the catheter 12 is in the second mode of operation, each of the sleeve electrodes 104, 106 is configured to switch between a conducting state and a non-conducting state. Switching circuitry to switch the electrodes 104, 106 between the conducting and non-conducting states may be integrated locally within the electrodes 104, 106, or may be electrically connected to the sleeve electrodes 104, 106 from a remote location. When in the conducting state, a sleeve electrode 104 or 106 is configured to conduct the RF heating energy to or from the RF electrode 14. When in a non-conducting state, the sleeve electrode 104 or 106 is electrically isolated from the flow of RF energy.

In FIG. 7A, the sleeve electrode 104 has been switched into a conducting state while the sleeve electrode 106 is in a non-conducting state. Accordingly, as illustrated, electric flux lines 108 extend between the RF electrode 14 and the conducting sleeve electrode 104. The sleeve electrode 106 is electrically isolated.

In FIG. 7B, the sleeve electrode 104 is switched into the non-conducting state, while the sleeve electrode 106 is switched into the conducting state. Accordingly, electrical energy is conducted between the RF electrode 14 and the conducting sleeve electrode 106, as depicted by the electric flux lines 110 shown in FIG. 7B. The sleeve electrode 104 is electrically isolated.

In this manner, by switching the sleeve electrodes 104, 106 between a conducting state and a non-conducting state, a variable volume of tissue in the patient may be treated. In addition to controlling the volume of heated tissue, selective switching of the sleeve electrodes 104, 106 between the conducting and non-conducting states also provides control over the temperature of the heated tissue as the flow of electrical energy through the variable tissue volumes is controlled.

As can be appreciated from the foregoing discussion, the volume of tissue destruction in the tissue 72 being treated may be controlled via a number of factors which can be chosen by design. These factors include the shape and size of the RF electrode 14; the spacing of electrode elements such as the conductive tip 18, the exposed portion 24 of the RF electrode 14, and the sleeve electrodes 100 or 104, 106; the use of electrical conduction-enhancing fluids; the length of exposure of the tissue to RF heating energy; the magnitude of the RF heating energy; the suppression of convective flow through the tissue 72; the number of electrodes; the choice of monopolar or bipolar mode of energy delivery; and/or the choice of electrical waveform and duty cycle in delivering the RF energy to the tissue.

In the discussion above, the catheter 12 is shown directly tunneling through the patient's tissue 70 into the tumor mass 72. In further embodiments, the catheter 12 may be transported internal to the patient tissue by way of an additional transport mechanism, such as a probe with or without visualization apparatus. For example, FIGS. 8A, 8B and 8C depict the delivery of a catheter 12 using a probe 120 with an integrated ultrasound transducer array 122. The transducer array 122 may be used to visualize the tissue to be treated. Once the probe 120 is properly positioned, the catheter 12 may be launched from an exit port in the probe 120 toward the tissue to be treated.

During initial delivery, as illustrated in FIG. 8A, the catheter 12 remains within the interior of the ultrasound probe 120 while the probe 120 is positioned near the tissue to be treated. To help position the probe 120 near the target tissue, separate visualization apparatus may be used to locate the tissue to be treated and place the probe 120 in an approximate nearby position. Such separate visualization apparatus may be an off-the-shelf ultrasound probe having a transducer array that provides a larger field of view relative to the transducer array 122 on the probe 120. Alternatively, the separate visualization apparatus may be a fluoroscope or other imaging apparatus capable of providing guidance for initial placement of the probe 120 relative to the tissue of the patient. In yet other circumstances where the catheter 12 is delivered directly without a transport mechanism such as the probe 120, visualization apparatus is still preferably used to guide the positioning of the catheter 12.

After placing the probe 120 in an approximate nearby position, the transducer array 122 on the probe 120 may be used to obtain a smaller but finer view of the tissue to be treated. With the finer imaging provided by the transducer array 122, the probe 120 can be properly positioned so that, when forward pressure is placed on the catheter 12, the catheter 12 will launch from the exit port of the probe 120 in the desired trajectory towards the tissue to be treated.

The exit port of the probe 120 may be placed within the transducer array 122, as depicted in FIG. 8A. Alternatively, from a manufacturing point of view, it may be better to position the exit port to the side of the transducer array 122 so as not to interrupt the layout of the array 122. The exit port may be placed either at the distal or proximal end of the transducer array 122.

The embodiment shown in FIG. 8A further depicts a deflecting mechanism 124 that redirects the catheter 12 from an axial to transverse trajectory relative to the probe 120 when the catheter 12 is advanced forward. The position of the deflector mechanism 124 may be fixed relative to the probe 120 so that the exit trajectory of the catheter 12 is always the same. In such an embodiment, the catheter 12 is directed out of the probe 120 in a desired direction by first placing the probe 120 in a desired position. If desired, pull wires may be connected to the distal end of the probe 120 to adjust the position of the probe after the probe has been inserted in the patient's body. The positioning of the probe 120 may be facilitated by providing one or more points of articulation in the probe 120. ATL/Philips of Bothell, Wash., for example, provides a steerable transesophageal probe that could be used as a basis for constructing the probe 120 and/or the catheter 12.

Alternatively, in the embodiment shown in FIGS. 8A-8C, the position of the deflecting mechanism 124 is adjustable relative to the probe 120. The position of the deflecting mechanism 124 may be adjusted to direct the catheter 12 in a desired trajectory when the catheter 12 advances out of the probe 120 and tunnels through the tissue 70 toward the tissue to be treated. In the illustrated embodiment, the deflector mechanism 124 is connected to a stiff lead wire 126 that can be selectively pulled or pushed by an operator of the probe 120 to position the deflector mechanism 124 with a desired curve. Thereafter, when a forward pressure is applied to the catheter 12 and RF sparking energy is delivered, the deflector mechanism 124 will direct the catheter 12 into the tissue 70 of the patient along a desired trajectory, as illustrated in FIG. 8B.

In at least one embodiment, the catheter 12 is flexible yet stiff enough to stay on a straight course once launched out of the exit port and tunneling through the tissue of the patient. Alternatively, the catheter 12 is constructed with pull wires inside the insulating sleeve 20 that permit active steering of the tip 18 at the time of launch of the catheter 12, as well as later during the RF tunneling through the patient's tissue. Under the guidance of ultrasonic visualization, such active steering of the catheter tip 18 can be used to fine tune the trajectory of the catheter 12 as it approaches a tumor or lesion to be treated. This allows for midcourse corrections of the penetration of the catheter system if the original launch direction was incorrect.

As a further alternative to pull wires in the catheter 12, active steering of the tip 18 may be obtained by connecting a bi-metal strip to the tip 18. Where the metals forming the bi-metal strip have different thermal expansion coefficients, the curvature of the bi-metal strip may be controlled by controlling the temperature of the strip. Because the bi-metal strip is connected to the tip 18, the variable curvature of the strip may be used to actively steer the tip 18.

As previously described, in the first mode of operation of the catheter 12 shown in FIG. 8B, RF sparking energy is delivered to the conductive tip 18. The RF energy produces sparks that erode the tissue of the patient and creates a tunnel through with the catheter 12 advances into the tissue 70 of the patient. Visualization apparatus, such as the ultrasound transducer 122, can be used to visualize the tissue surrounding the RF electrode of the catheter 12. If desired, images produced by the visualization apparatus may include track lines that visually indicate where the catheter 12 is headed in the patient's tissue. Such track lines may be superposed on an image of the target tissue provided by the visualization apparatus to help ensure that the catheter reaches the intended position within the tissue to be treated. More recently, three-dimensional ultrasound imaging has been shown to be helpful in visualizing tissue and treatment in a patient. Three-dimensional imaging may help ensure the catheter 12 is directing the RF therapy to the proper tissue 72 in the patient.

The particular embodiment shown in FIG. 8B includes a linear array ultrasound visualization system. Persons of ordinary skill in the art know how to construct and implement a linear array ultrasound system. Accordingly, further details of the linear ultrasound system need not be provided herein. One example of a linear ultrasound system is provided in U.S. Patent Application Publication No. 2006/0189972, which describes a linear ultrasound array that has been known and used commercially for several years, e.g., as exemplified by the AcuNav™ system of Siemens AG of Munich, Germany.

With other embodiments of the catheter 12, alternative apparatus for visualizing the tissue of the patient may be used. For example, insertion of the catheter 12 into tissue of a patient may be guided visually (e.g., hysteroscopically, laparoscopically, or by direct vision) or by fluoroscopy, computed tomography (CT), magnetic resonance imaging (MRI), etc. In yet another alternative embodiment, the catheter 12 and deflecting mechanism 124 may be piggybacked onto a commercially-available linear array catheter or probe to avoid unnecessary design and manufacturing cost of a custom-made probe 120. In circumstances where ultrasound imaging is used, it is also advantageous to provide a coupling gel or fluid that fills any space between the ultrasound transducer array and the tissue being imaged. Thus, the probe 120 may include one or more channels to convey such coupling gel or fluid to the interface between the ultrasound transducer 122 and the tissue 72 being imaged. Alternatively, the site of this interface may be immersed in coupling fluid or if the site of the interface is inside a body cavity, the cavity may be filled with coupling fluid, e.g., as described in co-owned U.S. patent application Ser. No. 11/831,048, filed Jul. 31, 2007, and incorporated by reference herein.

Once the catheter 12 has advanced through the tissue of the patient and is positioned within the tissue 72 to be treated, as shown in FIG. 8C, the insulating sleeve 20 of the catheter 12 is retracted as previously described, thus exposing a portion 24 of the RF electrode between the conductive tip 18 and the insulating sleeve 20. In the second mode of operation shown in FIG. 8C, RF non-sparking energy is conducted by the RF electrode 14 through the tissue 72 of the patient. This RF energy is capable of heating the tissue 72 surrounding the RF electrode for necrotization of the tissue without producing sparks. During the process of heating the tissue 72 to be treated, the visualization apparatus 122 may be configured to detect treatment-induced changes in the heated tissue 72 to track the progression of treatment of the tissue. For example, bubbles or vacuoles may be induced in the tissue 72 as a result of the destructive heating of the tissue. The presence of the bubbles or vacuoles is detected by the visualization apparatus 122 and may be used as a surrogate for tracking the coagulation and/or destruction of the unwanted tissue.

Alternative modes of tracking the progress of treatment of the tissue 72 may rely on detection of tissue temperature. For example, a temperature sensor may be used to detect the temperature of the tissue being treated. The temperature sensor (or sensors) may be mounted on the catheter 12 itself or alternatively on a needle probe that can be extended from the catheter 12 into the surrounding tissue. Yet other alternatives for monitoring the progress of the treatment may rely on temperature sensing MRI scans, blood flow reports via doppler ultrasound, tissue echogenicity via B-mode ultrasound, tissue elasticity via elastography, or acoustic radiation force impulse imaging; RF impedance of the surrounding tissue; and/or monitoring of cavitation via passive or active acoustic detectors.

Figure 9:
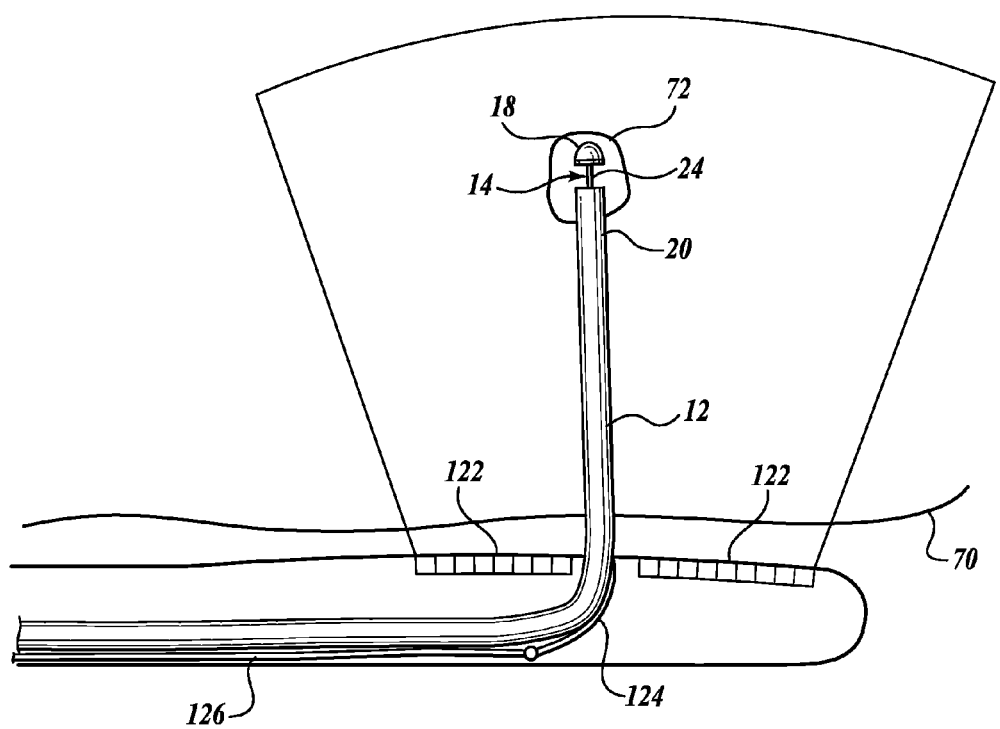
FIG. 9 illustrates the catheter of FIG. 8C in which the insulating sleeve is retracted a shorter distance for treating a smaller volume of tissue in the patient.

In addition, the visualization apparatus 122 may be operable to visualize the tissue surrounding the RF electrode 14 to assist in determining the desired portion 24 of the RF electrode to be exposed when conducting the second (treating) mode of operation of the catheter 12. Further depicted in FIG. 9 is an implementation where the insulating sleeve 20 is retracted from the tip 18, but not as far as depicted in FIG. 8C. With a smaller portion of the RF electrode 14 exposed to the tissue 72, the catheter 12 delivers RF energy to a smaller volume of surrounding tissue. Accordingly, by adjustably retracting the insulating sleeve 20 to a desired position, the volume of tissue 72 to be treated by the RF electrode 14 can be controlled. Through visualization of the surrounding tissue, the desired portion of the RF electrode to be exposed may be determined.

Visualization of the tissue being treated may further be used to help guide the therapy being provided to the patient. Different treatment regimens may be prescribed to adjust to different tissue characteristics observed by the visualization apparatus.

After subjecting the tissue 72 to treatment in the second mode of operation, the catheter 12 may be withdrawn from the treated tissue. Prior to fully withdrawing the catheter 12 from the treated tissue, it may be desirable to seal the tunnel in the tissue 72. One effect of this seal is to prevent the flow of fluids, such as a chemical adjuvant or debriding agent, out of the tunnel. In this circumstance, the catheter 12 may be operated to again deliver RF energy via the conductive tip 18. The RF energy is used to precipitate shrinkage of the patient's tissue and/or produce an area of coagulation at the exit of the tunnel, thus sealing the tunnel in the tissue. By depositing thermal energy at the exit of the tunnel, clotting factors in adjacent blood may plug the hole. Moreover, platelets tend to deposit themselves in a zone of damage such as thermal necrosis.

In yet another embodiment, after concluding treatment of the target tissue, the catheter 12 may apply a negative pressure to the tunnel in the tissue. The suction resulting from this negative pressure causes the tunnel to collapse and the tissue walls of the tunnel to pull together forming a seal. If desired, the exit of the tunnel could be "welded" shut by applying RF heating energy to the tissue at the exit, as described above. Again, this seal may prevent fluids deposited in the treated tissue from escaping out of the tunnel. The conveyance mechanism 62 shown in FIG. 1 may comprise a pump that could be used in conjunction with a lumen and port on the outside of the catheter 12 to provide the suction pressure to the tunnel in the tissue.

While illustrative embodiments have been depicted and described, it will be appreciated that various changes can be made therein without departing from the spirit and scope of the invention. For example, rather than using an ultrasound probe 120, the catheter 12 may initially be transported through the patient using an endoscope, laparoscope, or other transport mechanism to a position near the tissue to be treated. Such transport mechanisms are known in the art and can be guided in two or three dimensions to reach a desired position in the patient.

The catheter 12 could also be launched from a commercially-available needle guide, such as the type used for delivering a biopsy needle. The needle guide may be mechanically attached to or integrated with a probe having visualization apparatus that images the target tissue. These images may help point the needle guide in the proper direction toward the target tissue so that the catheter 12, when launched from the needle guide, is able to directly tunnel through the patient's tissue into the target tissue to be treated.

For example, U.S. Pat. No. 4,742,829, incorporated herein by reference, describes an ultrasound probe and needle guide that could be adapted to launch a catheter 12 as described herein. In one embodiment illustrated in FIG. 10, a probe 130 includes an elongated body 132 attached to a handle 134. A guide 136 is detachably mounted to the probe 130. When the guide 136 is mounted on the probe 130 as shown, a tongue 138 extending from a proximal end of the guide 136 fits into a corresponding groove 140 defined in the probe 130. A securing mechanism 142 toward a distal end of the guide 136 secures the guide 136 to the body 132, e.g., by a snap fit detent mechanism or other means of securing.

Figure 10:
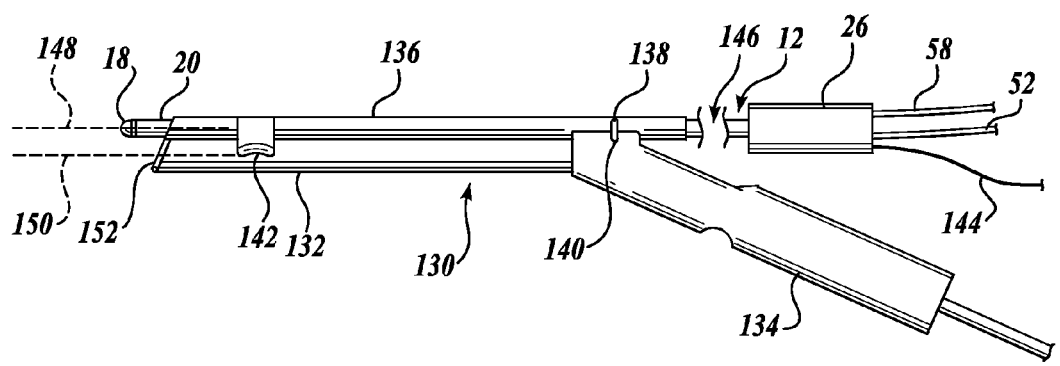
FIG. 10 illustrates a probe with a guide mounted thereon for receiving a catheter as described herein and directing the catheter into the tissue of a patient.

The guide 136 has a hollow core that permits the catheter 12 to extend therethrough. As with previous embodiments described herein, the catheter 12 has a tip 18 that conducts RF energy and a retractable sleeve 20. The catheter 12 may further have a handle 26, as well as first and second tubes 52, 58 for conveying fluids as previously described. An electrical lead 144 connects the catheter 12 to a source of RF energy. For ease of illustration, a break 146 is depicted in FIG. 10 to indicate that the full length of the catheter 12 is not necessarily depicted.

Once mounted, the guide 136 has an axis 148 aligned parallel to a central axis 150 of the probe body 132. The probe 130 is fitted with visualization apparatus 152, which may be, for example, an optical device or an ultrasound transducer assembly as described in U.S. Pat. No. 4,742,829, which has a forward-looking field of view in the direction that the guide 136 launches the catheter 12. Instead of launching a biopsy needle as described in U.S. Pat. No. 4,742,829, the guide 136 shown in FIG. 10 directs the catheter 12 toward the target tissue to be treated, guided by one or more images obtained by the visualization apparatus 152. In a first mode of operation, the catheter 12 is advanced through the tissue in the patient by conducting RF sparking energy to the tip 18 and applying forward pressure to the catheter 12. Once the catheter 12 is positioned within the target tissue to be treated, the RF sparking energy is terminated, the sleeve 20 is retracted, and RF heating energy is applied to the tissue, resulting in necrotization of the target tissue. The RF heating energy is then terminated and the catheter 12 is withdrawn from the patient.

As previously noted, various embodiments have been depicted and described herein. While these embodiments achieve a variety of benefits, patent protection obtained herewith should not be limited to the precise forms shown, but should be determined from the claims that follow and equivalents thereto.

We claim:

1. A catheter for insertion into tissue of a patient for treatment, comprising:
   a radio frequency (RF) electrode having an elongated body and a conductive tip at a distal end of the elongated body, wherein the elongated body is configured to conduct electrical RF energy to the conductive tip; and
   an insulating sleeve surrounding the elongated body of the RF electrode, wherein the insulating sleeve is configured to prevent electrical RF energy conducted by the elongated body from being transmitted by the elongated body to the tissue of the patient surrounding the elongated body when the catheter is being inserted into the tissue of the patient,
   wherein, in a first mode of operation for insertion of the catheter into the tissue of the patient, the conductive tip of the RF electrode is exposed outside the insulating sleeve and the RF electrode is configured to deliver, via the conductive tip, first RF energy capable of producing sparks that erode the tissue of the patient and create a tunnel through which the catheter can advance into the tissue of the patient, and
   wherein, in a second mode of operation for treatment of the tissue in the patient, the insulating sleeve is retractable to expose a portion of the RF electrode between the conductive tip and the insulating sleeve, and the RF electrode is configured to conduct second RF energy to the tissue in the patient, wherein the second RF energy is capable of heating the tissue surrounding the RF electrode for necrotization of the tissue without producing sparks.

2. The catheter of claim 1, wherein the insulating sleeve is adjustably retractable to expose a desired portion of the RF electrode in accordance with a desired volume of the tissue surrounding the RF electrode to be heated for necrotization.

3. The catheter of claim 2, further comprising visualization apparatus operable to visualize the tissue surrounding the RF electrode, wherein the desired portion of the RF electrode to be exposed is determined from visualization of the surrounding tissue.

4. The catheter of claim 1, further comprising visualization apparatus operable to visualize the tissue surrounding the RF electrode, wherein the visualization apparatus is configured to observe treatment-induced changes in the heated tissue to track the progression of treatment of the tissue.

5. The catheter of claim 1, further comprising a lumen configured to deliver a biocompatible electrically-resistant fluid that fills a volume around the RF electrode within the insulating sleeve when the catheter is in the first mode of operation.

6. The catheter of claim 1, further comprising a lumen configured to deliver a biocompatible electrically-conductive fluid that perfuses the tissue surrounding the exposed portion of the RF electrode to increase electrical conductivity of the tissue and enhance the volume of the tissue that is necrotized when the catheter is in the second mode of operation.

7. The catheter of claim 6, wherein the biocompatible fluid further comprises a thermally-activated chemical adjuvant configured to aid in necrotizing the tissue with reduced thermal dosage.

8. The catheter of claim 1, further comprising a multi-purpose lumen configured to selectively deliver a first biocompatible fluid in the first mode of operation and a second biocompatible fluid in the second mode of operation, wherein the first biocompatible fluid is an electrically-resistant fluid that fills a volume around the RF electrode within the insulating sleeve when the catheter is in the first mode of operation, and wherein the second biocompatible fluid is an electrically-conductive fluid that perfuses the tissue surrounding the exposed portion of the RF electrode when the catheter is in the second mode of operation, the second biocompatible fluid being configured to increase electrical conductivity of the tissue and enhance the volume of the tissue that is necrotized.

9. The catheter of claim 8, wherein the multi-purpose lumen is a first lumen, the catheter further comprising a second lumen configured to conduct fluid away from the tissue, wherein the second lumen cooperates with a conveyance mechanism for drawing the fluid away from the tissue.

10. The catheter of claim 1, further comprising a lumen configured to deliver a debriding agent that degrades the necrotized tissue.

11. The catheter of claim 1, further comprising a sleeve electrode disposed on the insulating sleeve, wherein in the second mode of operation, the insulating sleeve is retractable to expose a portion of the RF electrode between the conductive tip and the sleeve electrode and the RF electrode is configured to conduct the second RF energy to or from the sleeve electrode through the tissue in the patient.

12. The catheter of claim 11, wherein a plurality of sleeve electrodes are disposed on the insulating sleeve, and wherein, when the catheter is in the second mode of operation, each of the sleeve electrodes is configured for separate selective switching between a conducting state and a non-conducting state, wherein when in the conducting state a sleeve electrode is configured to conduct the second RF energy to or from the RF electrode, and when in a non-conducting state a sleeve electrode is electrically isolated from the second RF energy.

13. The catheter of claim 11, wherein the sleeve electrode is switchable to a non-conducting state in which the sleeve electrode is electrically isolated from RF energy conducted by the RF electrode.

14. The catheter of claim 1, further comprising one or more temperature sensors that are configured to sense the temperature of the surrounding tissue to guide the delivery of the second RF energy when the catheter is in the second mode of operation.

15. A combined guide and catheter for treatment of tissue in a patient, comprising:
   a catheter configured according to claim 1;
   a rigid guide having a hollow core, wherein the hollow core of the guide is sized to receive the catheter and allow the catheter to extend therethrough; and
   visualization apparatus configured to obtain an image of the tissue of the patient, wherein, in the first mode of operation, the catheter is extendable from a distal end of the guide into the tissue of the patient, the catheter creating a tunnel in the tissue of the patient in a direction determined by the position of the guide.

16. A method for inserting a catheter into tissue of a patient for treatment, comprising:
   positioning the catheter with respect to the tissue of the patient, wherein the catheter includes:
      a radio frequency (RF) electrode having an elongated body and a conductive tip at a distal end of the elongated body, wherein the elongated body is configured to conduct electrical RF energy to the conductive tip, and
      an insulating sleeve surrounding the elongated body of the RF electrode, wherein the insulating sleeve is configured to prevent electrical RF energy conducted by the elongated body from being transmitted by the elongated body to the tissue of the patient surrounding the elongated body when the catheter is being inserted into the tissue of the patient;
   positioning the insulating sleeve to expose the conductive tip of the RF electrode;
   delivering first RF energy to the conductive tip in a first mode of operation for insertion of the catheter into the tissue of the patient, wherein the first RF energy produces sparks that erode the tissue of the patient and creates a tunnel through which the catheter advances into the tissue of the patient; and
   while in a second mode of operation for treatment of the tissue of the patient, retracting the insulating sleeve to expose a portion of the RF electrode between the conductive tip and the insulating sleeve, and conducting second RF energy from the RF electrode to the tissue in the patient, wherein the second RF energy heats the tissue surrounding the RF electrode for necrotization of the tissue without producing sparks.

17. The method of claim 16, further comprising retracting the insulating sleeve by an adjustable amount to expose a desired portion of the RF electrode in accordance with a desired volume of the tissue surrounding the RF electrode to be heated for necrotization.

18. The method of claim 16, further comprising visualizing the tissue surrounding the RF electrode when in the second mode of operation, and adjusting the amount that the sleeve is retracted to expose a desired portion of the RF electrode in accordance with the visualized tissue.

19. The method of claim 16, further comprising visualizing the tissue surrounding the RF electrode when in the second mode of operation and tracking the progression of treatment of the tissue by observing treatment-induced changes in the heated tissue.

20. The method of claim 16, further comprising, when in the first mode of operation, delivering a biocompatible electrically-resistant fluid that fills a volume around the RF electrode within the insulating sleeve.

21. The method of claim 16, further comprising, when in the second mode of operation, delivering a biocompatible electrically-conductive fluid to the tissue surrounding the exposed portion of the RF electrode to increase electrical conductivity of the tissue and enhance the volume of the tissue that is necrotized.

22. The method of claim 21, further comprising delivering a debriding agent with the biocompatible fluid, wherein the debriding agent is configured to degrade the tissue that is necrotized.

23. The method of claim 16, further comprising selectively delivering a first biocompatible fluid and a second biocompatible fluid to the catheter, wherein the first biocompatible fluid is an electrically-resistant fluid that fills a volume around the RF electrode within the insulating sleeve when in the first mode of operation, and wherein the second biocompatible fluid is an electrically-conductive fluid that is delivered via the catheter to the tissue surrounding the exposed portion of the RF electrode to increase electrical conductivity of the tissue and enhance the volume of the tissue that is necrotized when in the second mode of operation.

24. The method of claim 21, further comprising conducting fluid away from the tissue via a lumen that cooperates with a conveyance mechanism for drawing the fluid away from the tissue.

25. The method of claim 16, wherein a sleeve electrode is disposed on the insulating sleeve, the method further comprising, when in the second mode of operation, retracting the insulating sleeve to expose a portion of the RF electrode between the conductive tip and the sleeve electrode and conducting the second RF energy to or from the sleeve electrode through the tissue in the patient.

26. The method of claim 25, further comprising switching the sleeve electrode to operate in a monopolar mode of operation in which the sleeve electrode is electrically isolated from the RF energy conducted by the RF electrode.

27. The method of claim 25, wherein a plurality of sleeve electrodes are disposed on the insulating sleeve, the method further comprising, when in the second mode of operation, selectively conducting the second RF energy between one or more of the sleeve electrodes and the RF electrode while electrically isolating non-conducting sleeve electrodes from the second RF energy.

28. The method of claim 16, further comprising sensing temperature of the surrounding tissue to guide the delivery of the second RF energy when the catheter is in the second mode of operation.

29. The method of claim 16, further comprising delivering a thermally-activated chemical adjuvant to the tissue surrounding the exposed portion of the RF electrode during or after the second mode of operation, wherein the adjuvant aids in necrotizing the tissue with reduced thermal dosage.

30. The method of claim 16, further comprising delivering a debriding agent to the tissue surrounding the exposed portion of the RF electrode during or after the second mode of operation, wherein the debriding agent aids in degrading the necrotized tissue.

31. The method of claim 16, further comprising:
withdrawing the catheter from the tissue that was treated in the second mode of operation; and
repeating a delivery of the first RF energy via the conductive tip to produce sparks that erode the tissue of the patient and produce an area of coagulation that seals the tunnel in the tissue that was treated and prevents flow of fluid out of the tunnel.

32. The method of claim 16, wherein positioning the catheter with respect to the tissue of the patient includes inserting the catheter into a hollow core of a rigid guide attached to a probe, wherein the probe further includes visualization apparatus that obtains an image of the tissue of the patient, the method further comprising positioning the guide with respect to the tissue of the patient in accordance with the obtained image, and, in the first mode of operation, extending the catheter from a distal end of the guide into the tissue of the patient, the catheter creating a tunnel in the tissue of the patient in a direction determined by the position of the guide.

* * * * *